US007826063B2

(12) United States Patent
Hill

(10) Patent No.: US 7,826,063 B2
(45) Date of Patent: Nov. 2, 2010

(54) COMPENSATION OF EFFECTS OF ATMOSPHERIC PERTURBATIONS IN OPTICAL METROLOGY

(75) Inventor: Henry A. Hill, Tucson, AZ (US)

(73) Assignee: Zygo Corporation, Middlefield, CT (US)

( * ) Notice: Subject to any disclaimer, the term of this patent is extended or adjusted under 35 U.S.C. 154(b) by 326 days.

(21) Appl. No.: 11/876,577

(22) Filed: Oct. 22, 2007

(65) Prior Publication Data

US 2008/0062405 A1 Mar. 13, 2008

Related U.S. Application Data

(63) Continuation of application No. PCT/US2006/044350, filed on Nov. 15, 2006, and a continuation-in-part of application No. 11/413,917, filed on Apr. 28, 2006, now Pat. No. 7,528,961.

(60) Provisional application No. 60/862,949, filed on Oct. 25, 2006, provisional application No. 60/676,190, filed on Apr. 29, 2005.

(51) Int. Cl.
*G01B 11/02* (2006.01)

(52) U.S. Cl. ...................................... 356/500
(58) Field of Classification Search .................. 356/500, 356/498, 486
See application file for complete search history.

(56) References Cited

U.S. PATENT DOCUMENTS

| 4,685,803 A | 8/1987 | Sommargren |
| 4,688,940 A | 8/1987 | Sommargren et al. |
| 4,733,967 A | 3/1988 | Sommargren |
| 4,948,254 A | 8/1990 | Ishida |
| 5,404,222 A | 4/1995 | Lis |
| 5,537,209 A | 7/1996 | Lis |
| 5,552,888 A | 9/1996 | Sogard et al. |
| 5,764,362 A | 6/1998 | Hill et al. |
| 5,838,485 A | 11/1998 | de Groot et al. |
| 6,137,574 A | 10/2000 | Hill |
| 6,198,574 B1 | 3/2001 | Hill |
| 6,201,609 B1 | 3/2001 | Hill |

(Continued)

FOREIGN PATENT DOCUMENTS

EP 0 843 152 5/1998

(Continued)

OTHER PUBLICATIONS

International Search Report for International Application No. PCT/US2006/043494 dated Mar. 20, 2008.

(Continued)

*Primary Examiner*—Tarifur Chowdhury
*Assistant Examiner*—Jonathon D Cook
(74) *Attorney, Agent, or Firm*—Fish & Richardson P.C.

(57) ABSTRACT

In general, in a first aspect, the invention features a method that includes using an interferometry assembly to provide three different output beams, each output beam including an interferometric phase related to an optical path difference between a corresponding first beam and a corresponding second beam, each first beam contacting a measurement object at least once, monitoring the interferometric phases for each of the three different output beams, and deriving information about variations in the optical properties of a gas in the first beam paths from the three monitored phases.

25 Claims, 9 Drawing Sheets

U.S. PATENT DOCUMENTS

| | | |
|---|---|---|
| 6,246,481 B1 | 6/2001 | Hill |
| 6,252,668 B1 | 6/2001 | Hill |
| 6,330,065 B1 * | 12/2001 | Hill ............................ 356/485 |
| 6,407,816 B1 | 6/2002 | de Groot et al. |
| 6,430,465 B2 | 8/2002 | Cutler |
| 6,495,847 B1 | 12/2002 | Asano et al. |
| 6,529,279 B2 | 3/2003 | de Groot et al. |
| 6,573,996 B1 * | 6/2003 | Deliwala et al. ............ 356/487 |
| 6,757,066 B2 | 6/2004 | Hill |
| 6,765,195 B1 | 7/2004 | Leviton |
| 6,775,009 B2 | 8/2004 | Hill |
| 6,778,280 B2 | 8/2004 | de Groot |
| 6,806,961 B2 | 10/2004 | Hill |
| 6,819,434 B2 | 11/2004 | Hill |
| 6,839,141 B2 | 1/2005 | Hill |
| 6,842,256 B2 | 1/2005 | Hill |
| 6,888,638 B1 | 5/2005 | Hill |
| 6,891,624 B2 | 5/2005 | Hill |
| 6,937,349 B2 | 8/2005 | Jones et al. |
| 6,950,192 B2 | 9/2005 | Hill |
| 7,012,700 B2 | 3/2006 | de Groot et al. |
| 7,038,850 B2 | 5/2006 | Chang et al. |
| 7,075,619 B2 | 7/2006 | Hill |
| 7,106,454 B2 | 9/2006 | de Groot et al. |
| 7,139,081 B2 | 11/2006 | de Groot |
| 7,268,888 B2 | 9/2007 | Hill |
| 7,280,223 B2 | 10/2007 | Hill |
| 7,280,224 B2 | 10/2007 | Hill |
| 7,283,248 B2 | 10/2007 | Hill |
| 7,362,446 B2 | 4/2008 | Van Der Pasch et al. |
| 7,528,961 B2 | 5/2009 | Hill |
| 2003/0048458 A1 | 3/2003 | Mieher et al. |
| 2003/0164948 A1 * | 9/2003 | Hill ............................ 356/487 |
| 2003/0179357 A1 | 9/2003 | Ravensbergen |
| 2004/0263846 A1 | 12/2004 | Kwan |
| 2005/0018162 A1 | 1/2005 | Leenders et al. |
| 2005/0151951 A1 | 7/2005 | Hill |
| 2006/0256346 A1 | 11/2006 | Hill |
| 2008/0285051 A1 | 11/2008 | Hill |

FOREIGN PATENT DOCUMENTS

| | | |
|---|---|---|
| JP | 64-18002 | 1/1989 |
| JP | 11-108614 | 4/1999 |
| JP | 11-230716 | 8/1999 |
| WO | WO 00/65302 | 11/2000 |

OTHER PUBLICATIONS

U.S. Appl. No. 60/862,949, filed Oct. 2006, Hill.
U.S. Appl. No. 60/859,348, filed Nov. 2006, Hill.
U.S. Appl. No. 60/859,693, filed Nov. 2006, Hill.
U.S. Appl. No. 60/869,483, filed Dec. 2006, Hill.
U.S. Appl. No. 60/869,482, filed Dec. 2006, Hill.
U.S. Appl. No. 10/218,968, filed Aug. 2002, Byoung-Sun Na.
Lis, Steven A.,"An Air Turbulence Compensated Interferometer For IC Manufacturing," SPIE 2440, [p. 467 (1995).
Arfken, G. "Gibbs Phenomenon", Mathematical Methods for Physicists, Academic Press (1966).
Bobroff, N., "Residual Errors In Laser Interferometry From Air Turbulence And Nonlinearity", Appl. Opt 26(13), pp. 907-926 (1987).
Bobroff, N., "Recent Advances In Displacement Measuring Interferometry," Measurement Science & Tech. 4(9), pp. 907-926 (1993).
Estler, W.T., "High-Accuracy Displacement Interferometry In Air," Appl. Opt. 24(6), pp. 808-815 (1985).
Jones, F.E., "The Refractivity Of Air", J. Res. NBS 86(1), pp. 27-32 (1981).
Ishida, Akira, "Two Wavelength Displacement-Measuring Interferometer Using Second-Harmonic Light To Eliminate Air-Turbulence-Induced Errors," Jpn. J. Appl. Phys. 28(3), L473-475 (1989).
Zanoni, C., "Differential Interferometer arrangements for distance and angle measurements: Principles, advantages and applications", VDI Berichte Nr. 749, pp. 93-106 (1989).
Zhu, Y. et al., "Long-Arm Two-Color Interferometer For Measuring The Change Of Air Refractive Index," SPIE 1319, Optics in Complex Systems, pp. 538-539 (1990).
International Preliminary Report on Patentability issued on Jun. 24, 2009, corresponding to Int'l. Appln. No. PCT/US2007/088708, filed Dec. 21, 2007.

* cited by examiner

COMPENSATION OF EFFECTS OF ATMOSPHERIC PERTURBATIONS IN OPTICAL METROLOGY

CROSS-REFERENCE TO RELATED APPLICATION

This application claims benefit of Provisional Patent Application No. 60/862,949, entitled "COMPENSATION OF EFFECTS OF ATMOSPHERIC PERTURBATIONS IN OPTICAL METROLOGY," filed on Oct. 25, 2006. This application is a continuation application of PCT/US2006/044350, entitled "COMPENSATION OF EFFECTS OF ATMOSPHERIC PERTURBATIONS IN OPTICAL METROLOGY," filed Nov. 15, 2006, which claims benefit of Provisional Patent Application No. 60/862,949. This application is also a continuation-in-part application of U.S. patent application Ser. No. 11/413,917, entitled "COMPENSATION OF TURBULENT EFFECTS OF GAS IN MEASUREMENT PATHS OF MULTI-AXIS INTERFEROMETERS," filed on Apr. 28, 2006, which claims benefit of Provisional Patent Application 60/676,190, entitled "COMPENSATION OF TURBULENT EFFECTS OF GAS IN MEASUREMENT PATHS OF MULTI-AXIS INTERFEROMETERS," filed on Apr. 29, 2005. The entire contents of all of the above-reference applications are incorporated herein by reference.

BACKGROUND

This disclosure relates to interferometry systems and methods of using interferometry systems, and particularly to monitoring and compensating effects of atmospheric perturbations in optical metrology applications of the interferometry systems.

Displacement measuring interferometers monitor changes in the position of a measurement object relative to a reference object based on an optical interference signal. The interferometer generates the optical interference signal by overlapping and interfering a measurement beam reflected from the measurement object with a reference beam reflected from the reference object.

In many applications, the measurement and reference beams have orthogonal polarizations and different frequencies. The different frequencies can be produced, for example, by laser Zeeman splitting, by acousto-optical modulation, or internal to the laser using birefringent elements or the like. The orthogonal polarizations allow a polarizing beam-splitter to direct the measurement and reference beams to the measurement and reference objects, respectively, and combine the reflected measurement and reference beams to form overlapping exit measurement and reference beams. The overlapping exit beams form an output beam that subsequently passes through a polarizer.

The polarizer mixes polarizations of the exit measurement and reference beams to form a mixed beam. Components of the exit measurement and reference beams in the mixed beam interfere with one another so that the intensity of the mixed beam varies with the relative phase of the exit measurement and reference beams.

A detector measures the time-dependent intensity of the mixed beam and generates an electrical interference signal proportional to that intensity. Because the measurement and reference beams have different frequencies, the electrical interference signal includes a "heterodyne" signal having a beat frequency equal to the difference between the frequencies of the exit measurement and reference beams. If the lengths of the measurement and reference paths are changing relative to one another, e.g., by translating a stage that includes the measurement object, the measured beat frequency includes a Doppler shift equal to $2vnp/\lambda$, where v is the relative speed of the measurement and reference objects, $\lambda$ is the wavelength of the measurement and reference beams, n is the refractive index of the medium through which the light beams travel, e.g., air or vacuum, and p is the number of passes to the reference and measurement objects. Changes in the phase of the measured interference signal correspond to changes in the relative position of the measurement object, e.g., a change in phase of $2\pi$ corresponds substantially to a distance change d of $\lambda/(2np)$. Distance 2d is a round-trip distance change or the change in distance to and from a stage that includes the measurement object. In other words, the phase $\Phi$, ideally, is directly proportional to d, and can be expressed as $\Phi=2pkd$, where $$k = \frac{2\pi n}{\lambda}.$$

Unfortunately, the observable interference phase, $\tilde{\Phi}$, is not always identically equal to phase $\Phi$. Many interferometers include, for example, non-linearities such as "cyclic errors." Cyclic errors can be expressed as contributions to the observable phase and/or the intensity of the measured interference signal and have a sinusoidal dependence on the change in for example optical path length 2pnd. In particular, a first order cyclic error in phase has for the example a sinusoidal dependence on $(4\pi pnd)/\lambda$ and a second order cyclic error in phase has for the example a sinusoidal dependence on $2(4\pi pnd)/\lambda$. Higher order cyclic errors can also be present as well as sub-harmonic cyclic errors and cyclic errors that have a sinusoidal dependence of other phase parameters of an interferometer system comprising detectors and signal processing electronics. Different techniques for quantifying such cyclic errors are described in commonly owned U.S. Pat. No. 6,137,574, U.S. Pat. No. 6,252,688, and U.S. Pat. No. 6,246,481 by Henry A. Hill.

In addition to cyclic errors, there are other sources of deviations in the observable interference phase from $\Phi$, such as, for example, non-cyclic non-linearities or non-cyclic errors. One example of a source of a non-cyclic error is the diffraction of optical beams in the measurement paths of an interferometer. Non-cyclic error due to diffraction has been determined for example by analysis of the behavior of a system such as found in the work of J.-P. Monchalin, M. J. Kelly, J. E. Thomas, N. A. Kurnit, A. Szöke, F. Zernike, P. H. Lee, and A. Javan, "Accurate Laser Wavelength Measurement With A Precision Two-Beam Scanning Michelson Interferometer," *Applied Optics*, 20(5), 736-757, 1981.

A second source of non-cyclic errors is the effect of "beam shearing" of optical beams across interferometer elements and the lateral shearing of reference and measurement beams one with respect to the other. Beam shears can be caused, for example, by a change in direction of propagation of the input beam to an interferometer or a change in orientation of the object mirror in a double pass plane mirror interferometer such as a differential plane mirror interferometer (DPMI) or a high stability plane mirror interferometer (HSPMI).

Inhomogeneities in the interferometer optics may cause wavefront errors in the reference and measurement beams. When the reference and measurement beams propagate collinearly with one another through such inhomogeneities, the resulting wavefront errors are identical and their contributions to the interferometric signal cancel each other out. More typically, however, the reference and measurement beam components of the output beam are laterally displaced from one another, i.e., they have a relative beam shear. Such beam shear causes the wavefront errors to contribute an error to the interferometric signal derived from the output beam.

Moreover, in many interferometry systems beam shear changes as the position or angular orientation of the measurement object changes. For example, a change in relative beam shear can be introduced by a change in the angular orientation of a plane mirror measurement object. Accordingly, a change in the angular orientation of the measurement object produces a corresponding error in the interferometric signal.

The effect of the beam shear and wavefront errors will depend upon procedures used to mix components of the output beam with respect to component polarization states and to detect the mixed output beam to generate an electrical interference signal. The mixed output beam may for example be detected by a detector without any focusing of the mixed beam onto the detector, by detecting the mixed output beam as a beam focused onto a detector, or by launching the mixed output beam into a single mode or multi-mode optical fiber and detecting a portion of the mixed output beam that is transmitted by the optical fiber. The effect of the beam shear and wavefront errors will also depend on properties of a beam stop should a beam stop be used in the procedure to detect the mixed output beam. Generally, the errors in the interferometric signal are compounded when an optical fiber is used to transmit the mixed output beam to the detector.

Amplitude variability of the measured interference signal can be the net result of a number of mechanisms. One mechanism is a relative beam shear of the reference and measurement components of the output beam that is for example a consequence of a change in orientation of the measurement object.

In dispersion measuring applications, optical path length measurements are made at multiple wavelengths, e.g., 532 nm and 1064 nm, and are used to measure dispersion of a gas in the measurement path of the distance measuring interferometer. The dispersion measurement can be used in converting the optical path length measured by a distance measuring interferometer into a physical length. Such a conversion can be important since changes in the measured optical path length can be caused by gas turbulence and/or by a change in the average density of the gas in the measurement arm even though the physical distance to the measurement object is unchanged.

The interferometers described above are often components of metrology systems in scanners and steppers used in lithography to produce integrated circuits on semiconductor wafers. Such lithography systems typically include a translatable stage to support and fix the wafer, focusing optics used to direct a radiation beam onto the wafer, a scanner or stepper system for translating the stage relative to the exposure beam, and one or more interferometers. Each interferometer directs a measurement beam to, and receives a reflected measurement beam from, e.g., a plane mirror attached to the stage. Each interferometer interferes its reflected measurement beams with a corresponding reference beam, and collectively the interferometers accurately measure changes in the position of the stage relative to the radiation beam. The interferometers enable the lithography system to precisely control which regions of the wafer are exposed to the radiation beam.

In many lithography systems and other applications, the measurement object includes one or more plane mirrors to reflect the measurement beam from each interferometer. Small changes in the angular orientation of the measurement object, e.g., corresponding to changes in the pitch and/or yaw of a stage, can alter the direction of each measurement beam reflected from the plane mirrors. If left uncompensated, the altered measurement beams reduce the overlap of the exit measurement and reference beams in each corresponding interferometer. Furthermore, these exit measurement and reference beams will not be propagating parallel to one another nor will their wave fronts be aligned when forming the mixed beam. As a result, the interference between the exit measurement and reference beams will vary across the transverse profile of the mixed beam, thereby corrupting the interference information encoded in the optical intensity measured by the detector.

To address this problem, many conventional interferometers include a retroreflector that redirects the measurement beam back to the plane mirror so that the measurement beam "double passes" the path between the interferometer and the measurement object. The presence of the retroreflector insures that the direction of the exit measurement is insensitive to changes in the angular orientation of the measurement object. When implemented in a plane mirror interferometer, the configuration results in what is commonly referred to as a high-stability plane mirror interferometer (HSPMI). However, even with the retroreflector, the lateral position of the exit measurement beam remains sensitive to changes in the angular orientation of the measurement object. Furthermore, the path of the measurement beam through optics within the interferometer also remains sensitive to changes in the angular orientation of the measurement object.

In practice, the interferometry systems are used to measure the position of the wafer stage along multiple measurement axes. For example, defining a Cartesian coordinate system in which the wafer stage lies in the x-y plane, measurements are typically made of the x and y positions of the stage as well as the angular orientation of the stage with respect to the z axis, as the wafer stage is translated along the x-y plane. Furthermore, it may be desirable to also monitor tilts of the wafer stage out of the x-y plane. For example, accurate characterization of such tilts may be necessary to calculate Abbé offset errors in the x and y positions. Thus, depending on the desired application, there may be up to five degrees of freedom to be measured. Moreover, in some applications, it is desirable to also monitor the position of the stage with respect to the z-axis, resulting in a sixth degree of freedom.

To measure each degree of freedom, an interferometer is used to monitor distance changes along a corresponding metrology axis. For example, in systems that measure the x and y positions of the stage as well as the angular orientation of the stage with respect to the x, y, and z axes, at least three spatially separated measurement beams reflect from one side of the wafer stage and at least two spatially separated measurement beams reflect from another side of the wafer stage. See, e.g., U.S. Pat. No. 5,801,832 entitled "METHOD OF AND DEVICE FOR REPETITIVELY IMAGING A MASK PATTERN ON A SUBSTRATE USING FIVE MEASURING AXES," the contents of which are incorporated herein by reference. Each measurement beam is recombined with a reference beam to monitor optical path length changes along the corresponding metrology axes. Because the different measurement beams contact the wafer stage at different locations, the angular orientation of the wafer stage can then be derived from appropriate combinations of the optical path length measurements. Accordingly, for each degree of freedom to be monitored, the system includes at least one measurement beam that contacts the wafer stage. Furthermore, as described above, each measurement beam may double-pass the wafer stage to prevent changes in the angular orientation of the wafer stage from corrupting the interferometric signal. The measurement beams may be generated from physically separate interferometers or from multi-axes interferometers that generate multiple measurement beams.

SUMMARY

An example of where an interferometer is used for high-precision measurements is to monitor the position of components in a lithography system. During the operation of such a system, the gas environment can frequently change. For example, introducing new wafers into the system causes gas movement in the system, as does removing them after exposure. Scanning or stepping the wafer and/or reticle during an exposure cycle can also cause gas movement in the system. In addition, temperature changes during an exposure cycle can affect environmental parameters like humidity and density, which can both affect gas refractivity. Furthermore, at different stages during an exposure cycle, the chamber can be flushed with various process gases, further disrupting the system's environment.

Because of these and other influences, the density, composition, temperature, and/or pressure of gas in the system can vary, giving rise to corresponding perturbations in the refractivity of the gas in the system. In addition, these perturbations in gas refractivity can occur at different times and at different locations in a lithography system during an exposure cycle. In such situations, the accuracy of interferometer measurements of the position and location of the wafer stage can be compromised if the refractivity variations associated with these perturbations to the environment are not accounted for.

In general, the perturbations occur with varying frequency depending on the source of the perturbation. For example, perturbations that occur due to gas turbulence have frequencies on the order of about 5 Hz (e.g., from about 1 to about 10 Hz). As another example, perturbations can occur as a result of acoustic modes that are excited in the interferometer environment (e.g., by movement of a wafer stage). The frequency of acoustic perturbations are related the speed of sound and the dimensions of the environment enclosing the interferometer. In lithography tools, acoustic perturbations typically occur with frequencies on the order of about 100 Hz (e.g., from about 50 Hz to about 200 Hz or more). Lower frequency perturbations can occur due to environmental effects (e.g., gas composition changes, temperature changes). Typically, these perturbations occur with frequencies of about 1 Hz or less (e.g., about 0.1 Hz or less).

In this disclosure, interferometric systems and methods are described for determining information about the effects of atmospheric perturbations on measurements made using an interferometer and compensating for these effects. The measurements include interferometric measurements of a change in linear and/or angular displacement of an object where perturbations in the refractivity of the gas are in the path of a measurement beam of the interferometer. The effects of the perturbations can be determined and compensated for one or more frequencies or ranges of frequencies, corresponding to different sources of perturbation. For example, embodiments can include determining and compensating for effects due to acoustic perturbations, turbulence, and/or environmental changes.

In certain embodiments, effects of gas refractivity perturbations are measured using an interferometry system that includes multiple parallel measurement axes. Simultaneous measurements along each axis are used to determine values of a parameter (e.g., a second difference parameter) that is insensitive to variations in the position of a measurement object along the axes and insensitive (at least to low order) to variations in the orientation of the measurement object with respect to the interferometer axes. Accordingly, ignoring other sources of errors in the measurements (e.g., mirror surface flatness errors, cyclic errors, non-cyclic errors), variations in the measured parameter can be attributed to the perturbations in gas refractivity in the measurement beam paths. Measurements of the parameter can be used to provide information about the gas refractivity perturbations. In particular, second and/or higher order spatial derivatives of the effects of variations in gas refractivity are measured with multiple-axes-per-plane interferometers where the predominant flow of the gas is in the plane of the multiple axes of the interferometer. The second and/or higher order spatial derivatives of the effects are integrated with respect to corresponding temporal and spatial coordinates to generate a contemporaneous measurement of gas refractivity perturbation effects on measurements of linear and angular displacements by the interferometers.

The effects on interferometer measurements due to perturbations at different frequencies can be determined by filtering the measurement parameter values (e.g., SDP) prior to integrating the spatial derivatives of the measured parameter. For example, a high pass filter (e.g., pass frequencies of about 100 Hz or more) can be used to determine effects due to acoustic perturbations, while a low pass filter (e.g., pass frequencies of about 10 Hz or less) can be used to determine effects due to turbulence.

Alternatively, or additionally, determining the effects of atmospheric perturbations from the SDP can involve making a frequency transform (e.g., a Fourier transform) of the SDP data, where the transform may be performed over a narrow pass band centered at a frequency of interest (e.g., a frequency corresponding to acoustic perturbations or turbulence).

In some embodiments, the methods include determining effects of stationary non-random systematic perturbations in addition to acoustic and/or turbulence perturbations.

Embodiments can include a combination of dispersive and non-dispersive techniques.

Information about gas refractivity perturbations can be used to correct for other measurements made using an interferometer, such as displacement measurements and/or orientation measurements of a measurement object. The corrections can be made contemporaneously and/or non-contemporaneously to acquiring the information about the gas refractivity variations.

In general, in a first aspect, the invention features a method that includes using an interferometry assembly to provide three different output beams, each output beam including an interferometric phase related to an optical path difference between a corresponding first beam and a corresponding second beam, each first beam contacting a measurement object at least once, monitoring the interferometric phases for each of the three different output beams, and deriving information about variations in the optical properties of a gas in the first beam paths from the three monitored phases.

Embodiments of the method can include one or more of the following features and/or features of other aspects.

The information can include a first contribution and a second contribution, the first and second contributions corresponding to variations in the optical properties of the gas at first and second frequencies, respectively. For example, the first frequencies can correspond to variations caused by turbulence in the first beam paths, and the second frequencies can correspond to variations caused by acoustic perturbations in the gas. For example, the first frequencies can be about 10 Hz or less, and the second frequencies can be about 100 Hz or more.

Deriving the information can include determining a parameter based on the monitored interferometric phases for the three different output beams and removing a contribution to the parameter due to variations in the optical properties of the gas having a particular range of frequencies. The contribution to the parameter due to the variations having the particular range of frequencies can be removed using a low pass filter. For example, the edge of the low pass filter can be at about 50 Hz or less, such as about 10 Hz or less. The contribution to the parameter due to the variations having the particular range of frequencies can be removed using a high pass filter. For example, the edge of the high pass filter can be at about 50 Hz or more, such as about 100 Hz or more. The removal of the contribution to the parameter can be achieved by a filtering process either prior to subsequent processing or during the subsequent processing for deriving the information.

Deriving the information can include determining a parameter based on the monitored interferometric phases for the three different output beams and determining a frequency transform of the parameter. For example, the frequency transform can be a Fourier transform. Deriving the information can include calculating properties of the frequency transform over a band of frequencies corresponding to variations in the information caused by turbulence in the first beam paths. Alternatively, for example, deriving the information can include calculating properties of the frequency transform over a band of frequencies corresponding to variations in the information caused by acoustic perturbations in the gas.

The interferometer assembly can define three interferometer axes and each interferometric phase includes information about a position of the measurement object along a corresponding one of the interferometer axes. The interferometer axes can be parallel. The interferometer axes can be coplanar.

Each of the first beams can contact the measurement object more than once (e.g., twice, three times, more than three times). Each of the first beams can contact the measurement object at a common location for at least one of the passes to the measurement object. In some embodiments, each of the second beams also contact the measurement object.

The variations in the optical properties of the gas can be caused by local refractivity variations that move through the first and/or the second beam paths. Variations in the three interferometric phases can be temporally correlated to the local refractivity variations.

The method can include monitoring a degree of freedom of the measurement object from one of the interferometric phases. Deriving the information can include reducing errors in the monitored degree of freedom, where the errors are related to the variations in the optical properties of a gas in the first beam paths. The errors can be reduced while the phases are being monitored. The degree of freedom can be a displacement of the measurement object along an interferometer axis defined by the interferometry assembly. In some embodiments, the degree of freedom is an orientation of the measurement object with respect to an interferometer axis defined by the interferometry assembly.

The method can further include reducing errors in the monitored degree of freedom due to stationary effects in the gas. Reducing the errors due to stationary effects of the gas can include monitoring a refractivity at a location within a chamber within which the measurement beams propagate and correcting the monitored degree of freedom based on the monitored refractivity and a non-trivial function mapping refractivity at the remote location to that in the measurement beams. Also, the method can further include monitoring variations in the optical properties of the gas using a dispersion interferometer and further reducing errors in the monitored degree of freedom based on the variations monitored with the dispersion interferometer.

Deriving the information can include determining values of a parameter from the monitored interferometric phases where, for a given position of the measurement object, the parameter is based on a difference between the position of the measurement object along a first interferometer axis and the position of the measurement object along a second interferometer axis parallel to the first interferometer axis, the first and second interferometer axes being defined by the interferometry assembly. The parameter can also be based on a difference between the position of the measurement object along the second interferometer axis and the position of the measurement object along a third interferometer axis parallel to the second interferometer axis, the third interferometry axis being defined by the interferometry assembly. Deriving the information can include determining values of a second difference parameter, SDP, from the monitored interferometric phases. A time average of the contributions of the variations of the optical properties of the gas to the second difference parameter can be zero. Deriving the information can further include determining a difference, $SDP_T$, between the second difference parameter value at time, t, and an average second difference parameter value. Furthermore, deriving the information can include integrating the difference $SDP_T$ over a time period. The integration can involve a product of the difference $SDP_T$ and a velocity of the variations in the optical properties of a gas through the first beam paths. The integration can provide information about a contribution, $\zeta$, to one of the monitored interferometric phases of the variations in the optical properties of the gas or a spatial derivative of $\zeta$.

The variations of the optical properties of the gas can be related to a local variation in the refractivity of the gas that moves non-parallel to the first beam paths as the local variation in the refractivity of the gas moves through the first beam paths.

In some embodiments, the method further includes using a lithography tool to expose a substrate supported by a moveable stage with radiation while interferometrically monitoring the position or orientation of the stage based on the derived information.

In general, in another aspect, the invention features a system that includes an interferometry assembly configured to provide three different output beams, each output beam including an interferometric phase related to an optical path difference between a corresponding first beam and a corresponding second beam, where the interferometry assembly directs each first beam to contact a measurement object at least once. The system further includes three detectors each positioned in a path of a corresponding output beam and an electronic processor coupled to the detectors, the electronic processor being configured to monitor the three interferometric phases and to derive information about variations in the optical properties of a gas in the measurement beam paths from the three monitored phases.

Embodiments of the system can include one or more of the following features and/or features of other aspects. The system can be configured to perform the methods of other aspects. The interferometry assembly can be configured to direct each of the first beams to contact the measurement object more than once. The interferometry assembly can be configured to direct each of the first beams towards the measurement object at a common location. In some embodiments, the interferometry assembly is configured to direct each of the second beams to contact the measurement object.

The measurement object can be a plane mirror measurement object. The interferometry assembly can define three different interferometer axes where the interferometric phase of each output beam corresponds to a position of the measurement object with respect to a corresponding one of the measurement axes. The interferometer axes can be parallel. In some embodiments, the interferometer axes are coplanar.

The system can include a stage that is moveable with respect to the interferometry assembly, where the measurement object is attached to the stage.

The system can further include a dispersion interferometer configured to monitor variations in the optical properties of the gas in the measurement beam paths. For example, the dispersion interferometer can be in communication with the electronic processor and the electronic processor is configured to determine a degree of freedom of the measurement object based on the variations in the optical properties of the gas monitored by the dispersion interferometer and from the information about variations in the optical properties of a gas in the measurement beam paths from the three monitored phases.

In another aspect, the invention features a lithography system for use in fabricating integrated circuits on a wafer. The lithography system includes the system of the aforementioned aspect, an illumination system for imaging spatially patterned radiation onto a wafer supported by the moveable stage, and a positioning system for adjusting the position of the stage relative to the imaged radiation. The interferometer assembly in the system is configured to monitor the position of the wafer relative to the imaged radiation and electronic processor is configured to use the information about to the variations in the optical properties of the gas to improve the accuracy of the monitored position of the wafer.

In another aspect, the invention features a beam writing system for use in fabricating a lithography mask. The beam writing system includes the system of the aforementioned aspect, a source providing a write beam to pattern a substrate supported by the moveable stage, a beam directing assembly for delivering the write beam to the substrate, a positioning system for positioning the stage and beam directing assembly relative one another. The interferometer assembly is configured to monitor the position of the stage relative to the beam directing assembly and electronic processor is configured to use the information about to the variations in the optical properties of the gas to improve the accuracy of the monitored position of the stage.

In general, in another aspect, the invention features methods that include interferometrically monitoring a distance between an interferometry assembly and a measurement object along each of three different measurement axes by directing three measurement beams along different paths between the interferometry assembly and the measurement object, determining values of a parameter at different times from the monitored distances, wherein for a given position of the measurement object the parameter is based on the distances of the measurement object along each of the three different measurement axes at the given position, and deriving information related to variations in the optical properties of a gas in the measurement beam paths from the parameter values.

Embodiments of the methods can include one or more of the following features and/or features of other aspect of the invention. Deriving the information can include determining a variation of the parameter value from an average parameter value. The average parameter value can correspond to an average of parameter values for the measurement object at the given position. Deriving the information can include integrating the variations of the parameter value over a time period. The method can include using the information related to the variations in the optical properties of the gas to improve the accuracy of measurements made using the interferometry assembly. The method can include using a lithography tool to expose a substrate with radiation passing through a mask while interferometrically monitoring the distance between the interferometry assembly and the measurement object, wherein the position of the substrate or the mask relative to a reference frame is related to the distance between the interferometry assembly and the measurement object. In some embodiments, the interferometer assembly or the measurement object are attached to a stage and at least one of the monitored distances is used to monitor the position of the stage relative to a frame supporting the stage.

In another aspect, the invention features lithography methods for use in fabricating integrated circuits on a wafer, where the methods include supporting the wafer on a moveable stage, imaging spatially patterned radiation onto the wafer, adjusting the position of the stage, and monitoring the position of the stage using the interferometry assembly and the measurement object and using the information related to variations in the optical properties of the gas in the measurement beam paths derived using the methods featured in other aspects of the invention to improve the accuracy of the monitored position of the stage.

In another aspect, the invention features lithography methods for use in the fabrication of integrated circuits that include directing input radiation through a mask to produce spatially patterned radiation, positioning the mask relative to the input radiation, monitoring the position of the mask relative to the input radiation using the interferometry assembly and the measurement object and using information related to variations in the optical properties of the gas in the measurement beam paths derived using the methods featured in other aspects of the invention to improve the accuracy of the monitored position of the mask, and imaging the spatially patterned radiation onto a wafer.

In a further aspect, the invention features lithography methods for fabricating integrated circuits on a wafer that include positioning a first component of a lithography system relative to a second component of a lithography system to expose the wafer to spatially patterned radiation, and monitoring the position of the first component relative to the second component using the interferometry assembly and the measurement object and using the information related to variations in the optical properties of the gas in the measurement beam paths derived using the methods featured in other aspects of the invention to improve the accuracy of the monitored position of the first component.

In a further aspect, the invention features methods for fabricating integrated circuits using the lithography methods featured in other aspects of the invention.

In another aspect, the invention features methods for fabricating a lithography mask, where the methods include directing a write beam to a substrate to pattern the substrate, positioning the substrate relative to the write beam, and monitoring the position of the substrate relative to the write beam using the measurement object and using the information related to variations in the optical properties of the gas in the measurement beam paths derived using the methods featured in other aspects of the invention to improve the accuracy of the monitored position of the substrate.

In general, in a further aspect, the invention features lithography systems for use in fabricating integrated circuits on a wafer, where the systems include a stage for supporting the wafer, an illumination system including a radiation source, a mask, a positioning system, a lens assembly, a first interferometry subsystem configured to monitor the position of the stage along a first axis, a second interferometry subsystem configured to monitor the position of the stage along a second axis orthogonal to the first axis, and a manifold for introducing a gas into the lithography system along a direction non-parallel to the first and second axes, wherein during operation the source directs radiation through the mask to produce spatially patterned radiation, the positioning system adjusts the position of the mask relative to the radiation from the source, the lens assembly images the spatially patterned radiation onto the wafer, and the first and second interferometry subsystems monitor the position of the mask relative to the radiation from the source.

Embodiments of the lithography systems can include one or more of the other features and/or features of other aspects of the invention. The manifold can introduce the gas into the lithography system along a direction that is at about 45 degrees with respect to the first axis. The manifold can introduce the gas into the lithography system along a direction that is at about 45 degrees with respect to the second axis. The first interferometry system can be configured to monitor the position of the stage along at least two other axes in addition to the first axis. The at least two additional axes can be parallel to the first axis. The at least two additional axes can be coplanar with the first axis.

In general, in another aspect, the invention features a method that includes using an interferometry assembly to monitor a degree of freedom of a stage in a lithography system while exposing a wafer to radiation using the lithography system. Monitoring the degree of freedom includes using an interferometry assembly to monitor an interferometric phase of three different output beams, each interferometric phase being related to a position of a stage with respect to a component of the interferometry assembly located away from the stage, deriving primary information about variations in the optical properties of a gas between the component and the stage, using a dispersion interferometer to determine secondary information about variations in the optical properties of the gas in the lithography system, and determining the degree of freedom of the stage based on at least one of the interferometric phases, the primary information, and the secondary information.

Embodiments of the method can include or more of the following features and/or features of other aspects. For example, determining the degree of freedom can include reducing uncertainty in the degree of freedom due to variations in the optical properties of the gas in the lithography system based on the primary and second information. The primary information can include information about variations in the optical properties of the gas that have a frequency of about 0.1 Hz or more. The primary information can include information about variations in the optical properties of the gas due to turbulence or acoustic perturbations. The secondary information can include information about variations in the optical properties of the gas that have a frequency of about 0.01 Hz or less. The secondary information can include information about variations in the optical properties of the gas due to stationary effects in the lithography system.

In general, in another aspect, the invention features a system, including an illumination apparatus for imaging spatially patterned radiation onto a wafer supported by a moveable stage, a positioning system for adjusting the position of the stage relative to the imaged radiation, and an interferometry system that includes an interferometry assembly configured to provide multiple different output beams, each output beam including an interferometric phase related to an optical path difference between a corresponding first beam and a corresponding second beam, where the interferometry assembly directs each first beam to contact a measurement object at least once. The interferometry system also includes multiple detectors each positioned in a path of a corresponding output beam and an electronic processor coupled to the detectors, the electronic processor being configured to monitor the three interferometric phases and to derive primary information about variations in the optical properties of gas in the path of the first beams from the three monitored phases. The interferometry system further includes a dispersion interferometer configured to provide secondary information about variations in the optical properties of the gas. The interferometry system is configured to monitor the position of the wafer relative to the imaged radiation and to use the information about the primary and secondary variations in the optical properties of the gas to improve the accuracy of the monitored position of the wafer. Embodiments of the system can include one or more of the features mentioned above in connection with other aspects.

Among other advantages, embodiments include interferometry systems and methods for making extremely accurate measurements of variations in displacement and/or orientation of a measurement object. Uncertainty in the measurements due to atmospheric perturbations can be reduced (e.g., by about 10 times or more, about 20 times or more) relative to conventional systems and methods.

Beams and/or axes referred to as being parallel or nominally parallel may deviate from being perfectly parallel to the extent that the effect of the deviation on a measurement is negligible (e.g., less than the required measurement accuracy by about an order of magnitude or more) or otherwise compensated.

Beams and/or axes referred to as being coplanar or nominally coplanar may deviate from being perfectly coplanar to the extent that the effect of the deviation on a measurement is negligible (e.g., less than the required measurement accuracy by about an order of magnitude or more) or otherwise compensated.

Beams and/or axes referred to as being orthogonal or nominally orthogonal may deviate from being perfectly orthogonal to the extent that the effect of the deviation on a measurement is negligible (e.g., less than the required measurement accuracy by about an order of magnitude or more) or otherwise compensated.

Unless otherwise defined, all technical and scientific terms used herein have the same meaning as commonly understood by one of ordinary skill in the art to which this invention belongs. A number of references are incorporated herein by reference. In case of conflict, the present specification will control.

Other features and advantages of the invention will be apparent from the following detailed description.

BRIEF DESCRIPTION OF THE DRAWINGS

FIG. 2b is a schematic plan view of the interferometry system shown in FIG. 1a.

Like reference symbols in the various drawings indicate like elements.

DETAILED DESCRIPTION

Figure 1A:
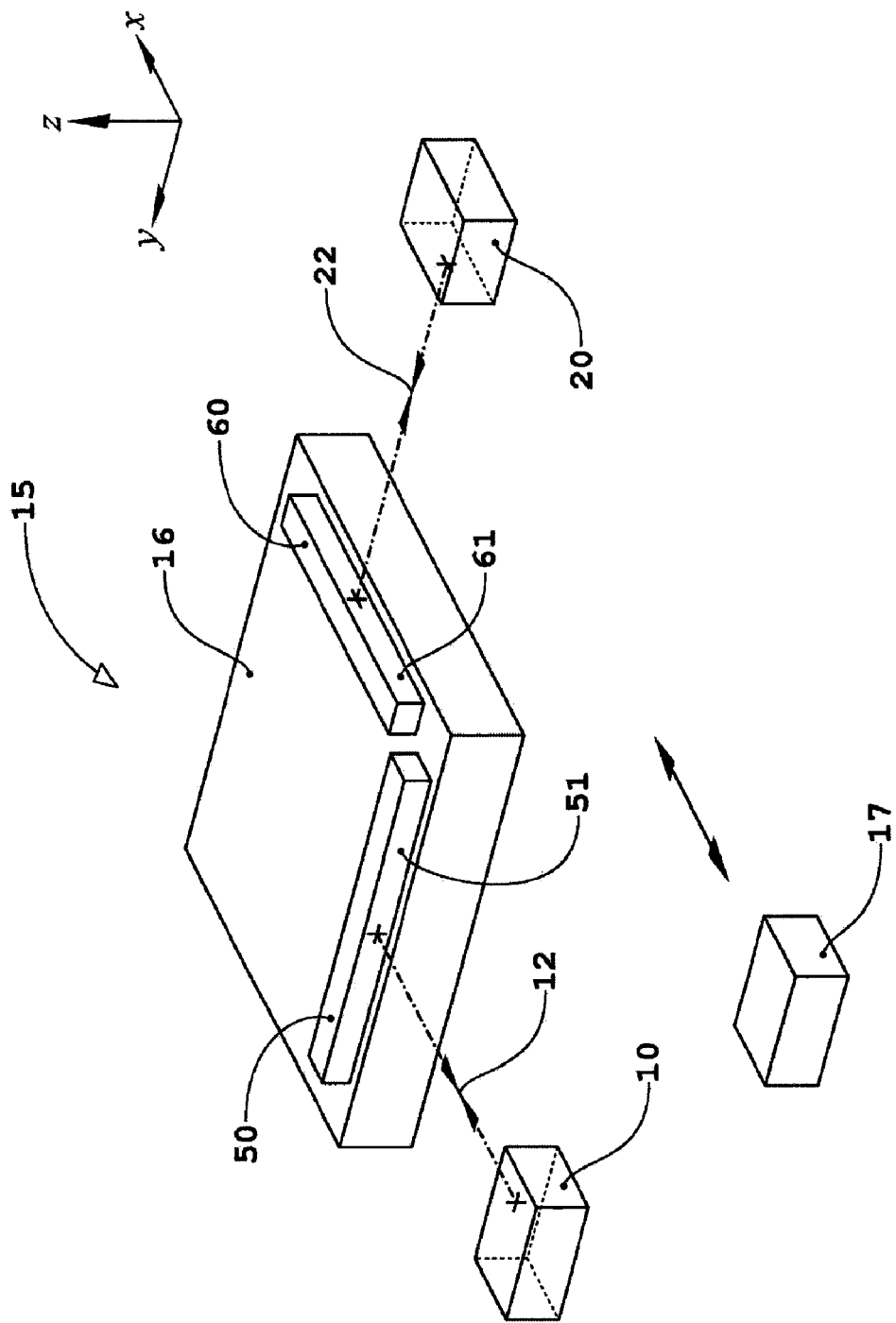
FIG. 1a is a schematic perspective view of an interferometer system that monitors the position of an object and compensates for effects of refractivity perturbations in a measuring path.

Reference is made to FIG. 1a which is a diagrammatic perspective view of an interferometric system 15 that employs a pair of orthogonally arranged interferometers or interferometer subsystems by which the shape of on-stage mounted stage mirrors may be characterized in situ with high spatial resolution along one or more datum lines and by which effects of a dispersive medium such as a gas in the measurement and/or reference beam paths may be compensated. As shown in FIG. 1a, system 15 comprises a stage 16 that forms part of a photolithographic apparatus for fabricating semiconductor products such as integrated circuits or chips. Affixed to stage 16 is a plane stage mirror 50 having a y-z reflective surface 51 elongated in the y-direction.

Also, fixedly mounted to stage 16 is another plane stage mirror 60 having an x-z reflective surface 61 elongated in the x-direction. Mirrors 50 and 60 are mounted on stage 16 so that their reflective surfaces, 51 and 61, respectively, are nominally orthogonal to one another. Stage 16 is otherwise mounted for nominally plane translation but may experience small angular rotations about the x, y, and z axes due to bearing and drive mechanism tolerances. In normal operation, system 15 is adapted to be operated for scanning in the y-direction for set values of x.

Fixedly mounted off-stage is an interferometer (or interferometer subsystem) that is generally indicated at 10. The purpose of interferometer 10 generally is to measure using non-dispersive interferometry the SDP of reflecting surface 51 and of the gas in the measurement beam paths of interferometer 10 and to measure the position of stage 16 in the x-direction and the angular rotations of stage 16 about the y- and z-axes as stage 16 translates in the y-direction. Interferometer 10 comprises two 3 axes/plane interferometers such as interferometer 100 shown in FIG. 1a and arranged so that interferometric beams travel to and from mirror 50 generally along an optical path designated as 12.

Also fixedly mounted off-stage is an interferometer (or interferometer subsystem) that is generally indicated at 20. The purpose of interferometer 20 generally is to measure using non-dispersive interferometry the SDP of reflecting surface 61 and of the gas in the measurement beam paths of interferometer 20, the position of stage 16 in the y-direction, and the angular rotations of stage 16 about the x- and z-axes as stage 16 translates in the x-direction in addition to other information such as used in mapping surface 61 of mirror 60. Interferometer 20 comprises two 3 axes/plane interferometers such as interferometer 100 shown in FIG. 1a and arranged so that interferometric beams travel to and from mirror 60 generally along an optical path designated as 22.

In some embodiments, interferometer subsystems 10 and 20 include apparatus and methods of dispersive interferometry in combination with apparatus and methods of non-dispersive techniques for the compensation of effects of a dispersive medium such as a gas in the measurement and/or reference beam paths of the respective interferometer subsystems 10 and 20. Interferometer subsystems 10 and 20 may comprise_a wavelength monitor or monitors and apparatus of dispersion interferometry such as a two wavelength source and a monitor for measurement of an intrinsic property of a gas such as the reciprocal dispersive power in interferometry subsystem 15.

Disclosed embodiments relate to apparatus and methods by which a change in a measurement and or reference beam path may be quickly measured and used in contemporaneous applications or in non-contemporaneous applications wherein either or both the refractivity of a gas in the measurement path and/or the physical length of the measurement path may be changing. An example of a contemporaneous application is in an interferometric angle and/or distance measuring instrument to enhance accuracy by compensating for gas environmental, stationary, turbulence, and acoustic perturbation effects on the refractivity of the gas in the measurement and/or reference beam paths, especially changes in the measurement and reference beam paths that take place during the measuring period because of gas turbulence and acoustic perturbation effects induced in the measurement and reference beam paths by rapid stage slew rates. An example of a non-contemporaneous application is an interferometric angle and/or linear displacement measuring instrument to enhance accuracy of compensating for gas environmental, stationary, turbulence, and acoustic perturbation effects in determination of alignment mark locations.

Dispersion and Non-Dispersion Interferometry

The frequency domains of the environmental, gas turbulence, and acoustic perturbation effects typically fall into well separated regions. For the turbulence effects, the corresponding frequency domain is generally determined by dimensions of the turbulent cells and the speed of transport of the cells through the measurement and/or reference beams. For the example of a turbulence generated cell with a characteristic dimension of 0.04 m and an gas flow speed perpendicular to the axes of the measurement and/or reference beams of 0.2 m/s, the corresponding frequency is of the order of 5 Hz.

The frequency domain of an acoustic perturbation except for an initial acoustic pulse generated by an acceleration of a measurement object will be determined primarily by the normal mode spectrum of a cavity containing interferometer system 15. For the example of interferometer system 15 located in a litho tool with characteristic dimensions of 1.5 m, the normal mode spectrum of the litho tool will comprise a fundamental mode with a frequency of approximately 200 Hz and harmonic modes thereof. Environmental effects of the gas generally generate changes in the optical path lengths with frequencies ~1 Hz.

Disclosed embodiments can employ combinations of different techniques to compensate for effects of the gas in the various frequency domains.

Non-Dispersion Interferometry

Non-dispersive interferometry used for the compensation of certain of the effects of a gas in the measurement and/or reference beam paths is based on interferometric measurements using measurement beams at a single optical wavelength. The non-dispersive techniques are based on the measurement of either the effects of the gas on the direction of propagation of a beam and/or on the effects of the gas on the optical path length experienced by a beam. Examples of non-dispersive techniques are disclosed in U.S. application Ser. No. 11/413,917 entitled "COMPENSATION OF TURBULENT EFFECTS OF GAS IN MEASUREMENT PATHS OF MULTI-AXIS INTERFEROMETERS" and filed Apr. 28, 2006, which claims priority to U.S. Application Ser. No. 60/676,190 of the same name, filed Apr. 29, 2005. The entire contents of both of these applications are hereby incorporation by reference in their entirety.

Figure 2A:
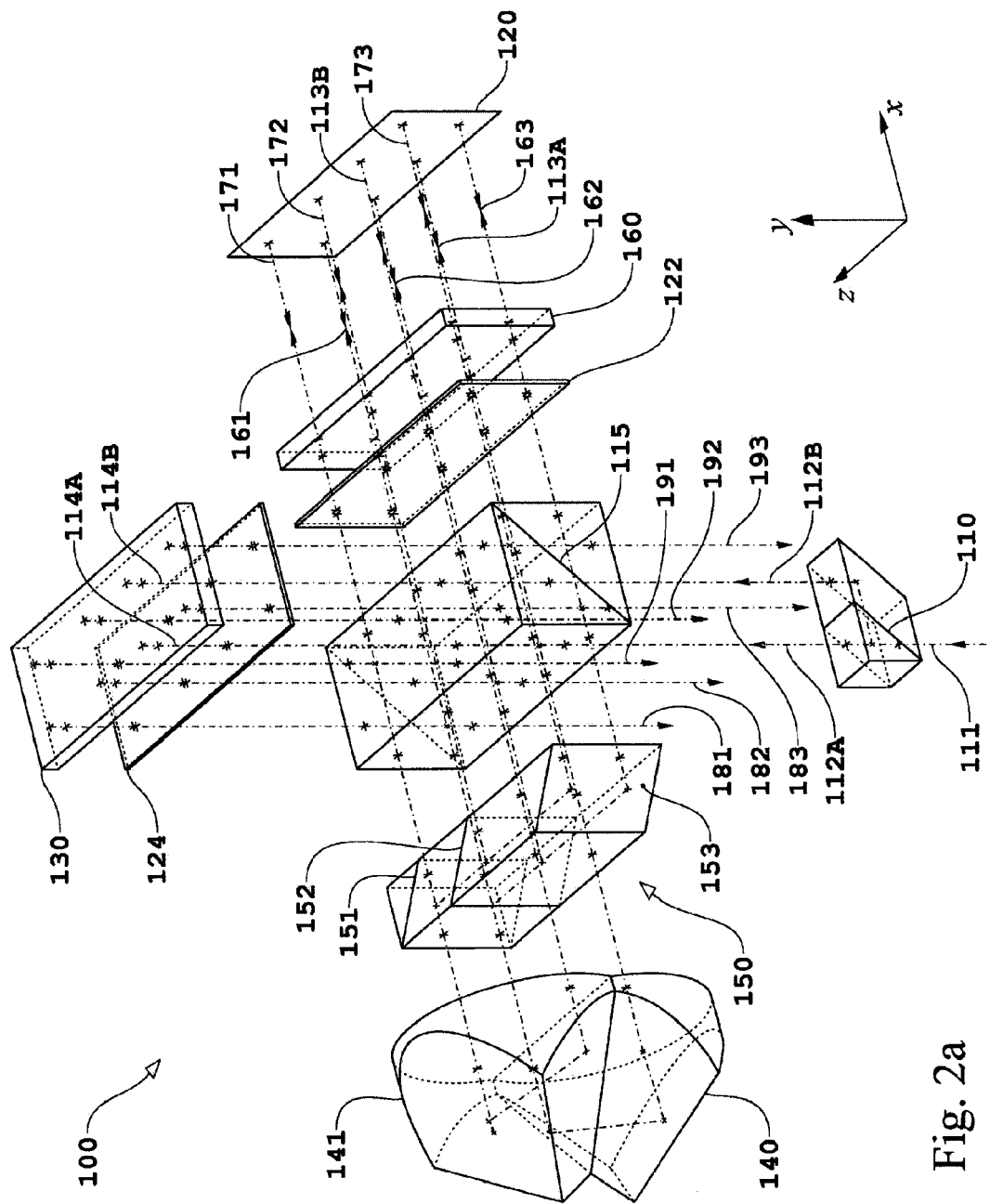
FIG. 2a is an exploded perspective view of an interferometer system comprising two three-axes-per-plane interferometers.
Figure 2B:
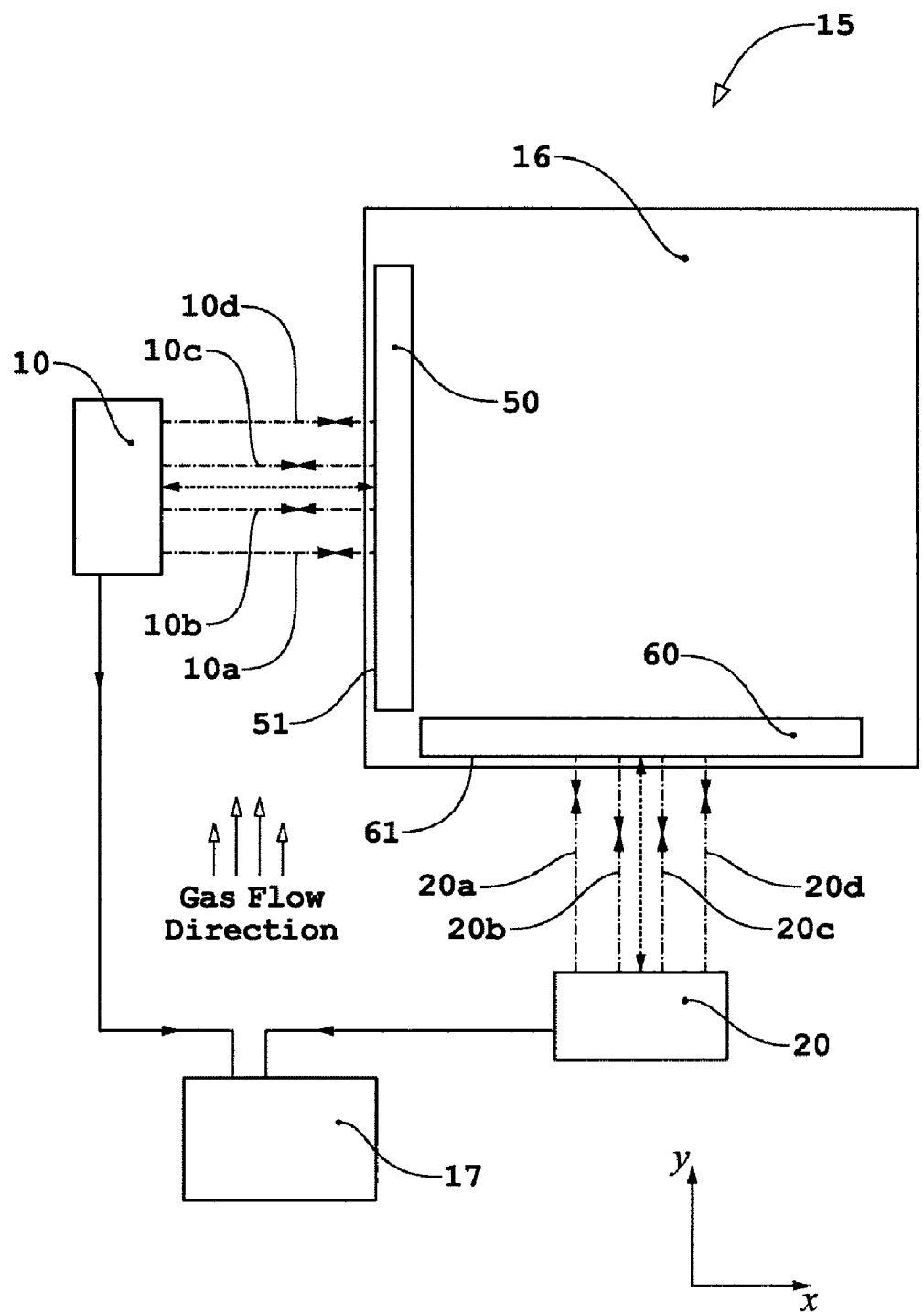

FIG. 2a shows an embodiment of a multiple-axes/plane plane mirror interferometer 100 that measures the effects of the gas on the optical path length experienced by a beam. The orientation of interferometer 100 with respect to the Cartesian co-ordinate system is optimal for situations where the predominant gas flow direction is parallel to the z-axis. The interferometer directs multiple measurement beams to each contact a measurement object 120 twice. For example, the measurement object may be a stage mirror for a wafer stage in a microlithography system. Interferometer 100 produces multiple output beams 181-183 and 191-193 each including interferometric information about changes in distance between the interferometry system and the measurement object along a corresponding measurement axis.

Interferometer 100 has the property that the output beams each includes a measurement component that makes one pass to the measurement object along a common measurement beam path before being directed along separate measurement beam paths for the second pass to the measurement object. Accordingly, the interferometer is similar to those disclosed in commonly owned U.S. patent application Ser. No. 10/351, 708 by Henry, A. Hill and entitled "MULTIPLE DEGREE OF FREEDOM INTERFEROMETER." The contents of patent application Ser. No. 10/351,708 are incorporated herein in their entirety by reference. Interferometer 100 is different from those disclosed in the cited reference in that it provides three measurement axes in a common plane, a feature that can be used to provide surface information about the measurement object independent of its angular orientation with respect to an axis perpendicular to the common plane such as described in commonly owned U.S. Pat. No. 6,757,066 entitled "MULTIPLE DEGREE OF FREEDOM HIGH STABILITY PLANE MIRROR INTERFEROMETER;" U.S. Provisional Patent Applications No. 60/534,481 entitled "MULTI-AXIS INTERFEROMETER FOR MIRROR MAPPING," No. 60/535,078 entitled "MULTI-AXIS INTERFEROMETER FOR MIRROR MAPPING," No. 60/564,448 entitled "MULTI-AXIS INTERFEROMETER AND DATA PROCESSING FOR MIRROR MAPPING," and No. 60/644, 898 entitled "MULTI-AXIS INTERFEROMETER AND DATA PROCESSING FOR MIRROR MAPPING;" and U.S. patent application Ser. No. 11/030,755 entitled "MULTI-AXIS INTERFEROMETER FOR MIRROR MAPPING," Ser. No. 11/112,375 entitled "MULTI-AXIS INTERFEROMETER AND DATA PROCESSING FOR MIRROR MAPPING," and Ser. No. 11/112,681 entitled "MULTI-AXIS INTERFEROMETER AND DATA PROCESSING FOR MIRROR MAPPING." The provisional applications No. 60/564,448 and No. 60/644,898 and the utility application Ser. No. 11/112,375 and Ser. No. 11/112,681 are by Henry A. Hill and Gary Womack and the remaining cited patent, provisional applications, and utility applications are by Henry A. Hill. The contents of the cited patent, provisional applications, and the utility applications are hereby incorporated herein in their entirety by reference.

In the described embodiment, interferometer 100 includes a non-polarizing beam splitter 110, which splits a primary input beam 111 into two secondary input beams 112A and 112B. Interferometer 100 also includes a polarizing beam splitter 115, which splits secondary input beams 112A and 112B into primary measurement beams 113A and 113B, and primary reference beams 114A and 114B, respectively. Interferometer 100 directs primary measurement beams 113A and 113B along paths that contact measurement object 120 at different locations in a vertical direction. Similarly, primary reference beams 114A and 114B are directed along reference beam paths that contact a reference mirror 130 at different locations. Interferometer 100 also includes quarter wave plates 122 and 124. Quarter wave plate 122 is located between polarizing beam splitter 115 and measurement object 120, while quarter wave plate 124 is located between polarizing beam splitter 115 and the reference mirror. The quarter wave plates rotate by 90° the polarization state of double passed beams directed between the polarizing beam splitter and the measurement object or reference mirror. Accordingly, the polarizing beam splitter transmits an incoming beam that would have been reflected in its out-going polarization state.

The following description pertains to primary measurement beam 113A and primary reference beam 114A. Interferometer 100 directs measurement beam 113B and reference beam 114B along analogous paths. Polarizing beam splitter (PBS) 115 transmits reflected primary measurement beam 113B, which is reflected back towards PBS 115 by a retroreflector 140 (a similar retroreflector 141 reflects primary measurement beam 113B). A compound optical component 150 including non-polarizing beam splitters 151 and 152 and reflector 153 split primary measurement beam 113A into three secondary measurement beams 161, 162, and 163. PBS 115 transmits the three secondary measurement beams, which propagate along paths that contact measurement object 120 at three different positions in a horizontal plane shared by primary measurement beam 113A. PBS 115 then directs the three secondary measurement beams reflected from measurement object 120 along output paths.

PBS 115 reflects primary reference beam 114A towards retroreflector 140. As for the primary measurement beam, optical component 150 splits primary reference beam 114A reflected by retroreflector 140 into three secondary reference beams 171, 172, and 173. PBS 115 reflects secondary reference beams 171, 172, and 173 towards reference mirror 130 along paths at three different positions in a plane shared by primary reference beam 114A. PBS 115 transmits secondary reference beams 171, 172, and 173 reflected from reference object 130 along output paths so that they overlap with measurement beams 161, 162, and 163 to form output beams 181, 182, and 183, respectively. The phase of the output beams carries information about the position of the measurement object along three measurement axes defined by the primary measurement beam's path and the secondary measurement beams' paths.

Interferometer 100 also includes a window 160 located between quarter wave plate 122 and measurement object 120.

Figure 1B:
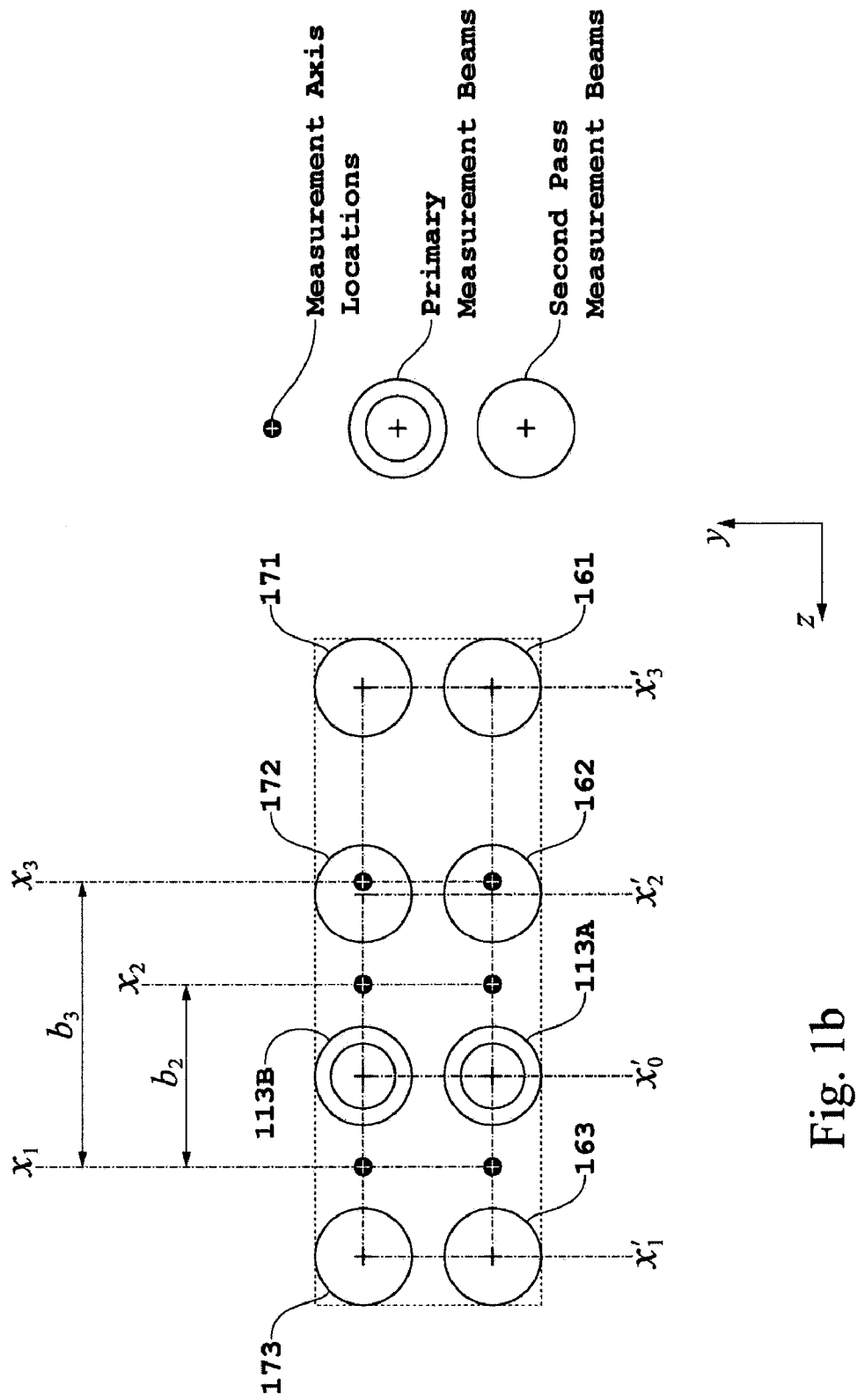
FIG. 1b is a diagram that shows the pattern of measurement beams from interferometer system of FIG. 1a at a stage mirror that serves as measurement object for interferometers of the interferometer system.

The pattern of measurement beams incident on a respective stage mirror is shown in FIG. 1b with the angle of incidence of measurement beams at the stage mirror nominally zero and for the example of measurement axes parallel to the x-axis of a coordinate system. The locations of the measurement axes of the top multiple-axes/plane interferometer corresponding to $x_1$, $x_2$, and $x_3$ are shown in FIG. 1b. The spacings between measurement axes corresponding to $x_1$ and $x_2$ and to $x_1$ and $x_3$ are $b_2$ and $b_3$, respectively. Also shown in FIG. 1b is the location corresponding to the primary single pass measurement beam $x_0'$ and the locations corresponding to the second pass measurement beams $x_1'$, $x_2'$, and $x_3'$. The plane of the measurement axes corresponding to $x_1$, $x_2$, and $x_3$ is shown in FIG. 1b as coplanar with the x-y plane of the coordinate system indicated in FIG. 1b. In certain litho tools where the gas flow is arranged to be predominately in the z direction, the plane of the measurement axes corresponding to $x_1$, $x_2$, and $x_3$ is aligned so as to be coplanar with the z-x plane. More generally, the three measurement axes can be oriented in a plane parallel to the predominant gas flow direction, allowing the system to determine information about air turbulence effects using the methods set forth below.

The relationship between a linear displacement measurement corresponding to a double pass to the stage mirror and the linear displacement measurements corresponding to a single pass to the stage mirror is $$x_j = \frac{1}{2}(x'_j + x'_0), \, j = 1, 2, \text{ and } 3. \tag{1}$$

An important property of the multiple-axes/plane interferometer is that the difference between two linear displacements $x_i$ and $x_j$, $i \neq j$, is an independence of $x_0'$, i.e., $$x_i - x_j = \frac{1}{2}(x'_i - x'_j), \, i, j = 1, 2, \text{ and } 3, \, i \neq j. \tag{2}$$

The second difference parameter SDP is defined for a 3 axes/plane interferometer such that it is not sensitive to either a displacement of a respective stage mirror or to the rotation of the stage mirror except through a third order effect involving the angle of stage rotation in a plane defined by the 3 axes/plane interferometer and departures of the stage mirror surface from a plane. The third order effect is classified as such since it is generated by a geometric effect that is second order in the angle of rotation of the stage mirror and a first order effect in the local apparent rotation of a section of the stage mirror due to the departures of the stage mirror surface from a plane. Different combinations of displacement measurements $x_1$, $x_2$, and $x_3$ may be used in the definition of a SDP. One definition of a SDP for an x-axis stage mirror is for example $$SDP(y) \equiv (x_2 - x_1) - \frac{b_2}{b_3 - b_2}(x_3 - x_2) \tag{3}$$

or $$SDP(y) = (x_2 - x_1) - \eta(x_3 - x_2) \tag{4}$$

where $$\eta \equiv \frac{b_2}{b_3 - b_2}. \tag{5}$$

A property of SDP is that it can be written in terms of single pass displacements using Eq. (2), i.e., $$SDP(y) = \frac{1}{2}[(x'_2 - x'_1) - \eta(x'_3 - x'_2)]. \tag{6}$$

Certain of the properties of the 3 axes/plane interferometer relevant to measurement of values of SDP are listed below.

SDP is independent of a displacement of the stage mirror for which SDP is being measured.

SDP is independent of a rotation of the stage mirror for which SDP is being measured except through a third order effect.

SDP is independent of properties of the primary single pass measurement beam path $x_0'$ in a 3 axes/plane interferometer used to measure the SDP.

SDP is independent of properties of the retroreflector in a 3 axes/plane interferometer used to measure the SDP.

SDP is independent of changes in the average temperature of a 3 axes/plane interferometer used to measure the SDP.

SDP is independent of linear temperature gradients in a 3 axes/plane interferometer used to measure the SDP.

SDP is independent of linear spatial gradients in the refractive indices of certain components in a 3 axes/plane interferometer used to measure the SDP.

SDP is independent of linear spatial gradients in the refractive indices and/or thickness of cements between components in a 3 axes/plane interferometer used to measure the SDP.

SDP is independent of "prism effects" introduced in the manufacture of components of a 3 axes/plane interferometer used to measure the SDP.

SDP is based on measurements of path lengths corresponding to single pass measurement beams.

A 3 axes/plane interferometer may be configured so that the linear displacements measured by the 3 axes/plane interferometer are not affected by certain spatial frequency components of the surface figure error function of a corresponding stage mirror for which SDP is not sensitive.

SDP for the x-axis stage mirror are measured as a function of position of the x-axis stage mirror in the y-direction with the corresponding x-axis location and the stage mirror orientation nominally held at fixed values. Also SDP for the y-axis stage mirror are measured as a function of position in the x-direction of the y-axis stage mirror with the corresponding y-axis location and stage orientation nominally held at fixed values. Increased sensitivity to high spatial frequency components of the surface figure of a stage mirror is obtained by measuring the respective SDP with the stage oriented at large pitch angles and large measurement path lengths to the stage mirror, i.e., for large measurement beam shears at the respective measuring 3 axes/plane interferometer.

The measurements of the respective SDP for the x-axis and y-axis stage mirrors do not require monitoring of changes in stage orientation during the respective scanning of the stage mirrors other than to maintain the stage at a fixed nominal value since SDP is independent of stage mirror orientation except for third order effects.

The values of SDP can be measured either during the normal processing cycle of wafers and/or during periods other than a normal processing cycle of wafers and/or prior to installation of the stage mirrors in a lithography tool. Cyclic errors that are present in the linear displacement measurements are eliminated and/or compensated by use of one of more techniques such as described in commonly owned U.S. patent application Ser. No. 10/097,365 entitled "CYCLIC ERROR REDUCTION IN AVERAGE INTERFEROMETRIC MEASUREMENTS" and Ser. No. 10/616,504 entitled "CYCLIC ERROR COMPENSATION IN INTERFEROMETRY SYSTEMS," which claims priority to U.S. Provisional Application No. 60/394,418 entitled "ELECTRONIC CYCLIC ERROR COMPENSATION FOR LOW SLEW RATES." Each of the utility applications and the provisional patent application are all by Henry A. Hill and the contents of each thereof are incorporated herein in their entireties by reference.

An example of another cyclic error compensation technique is described in commonly owned U.S. patent application Ser. No. 10/287,898 entitled "INTERFEROMETRIC CYCLIC ERROR COMPENSATION" which claims priority to U.S. Provisional Application No. 60/337,478 entitled "CYCLIC ERROR COMPENSATION AND RESOLUTION ENHANCEMENT." The utility application and the provisional patent application are each by Henry A. Hill and the contents thereof are incorporated herein in their entireties by reference.

Another example of a cyclic error compensation technique is described in U.S. patent application Ser. No. 10/174,149 entitled "INTERFEROMETRY SYSTEM AND METHOD EMPLOYING AN ANGULAR DIFFERENCE IN PROPAGATION BETWEEN ORTHOGONALLY POLARIZED INPUT BEAM COMPONENTS" which claims priority to U.S. Provisional Patent Application 60/303,299 entitled "INTERFEROMETRY SYSTEM AND METHOD EMPLOYING AN ANGULAR DIFFERENCE IN PROPAGATION BETWEEN ORTHOGONALLY POLARIZED INPUT BEAM COMPONENTS." The utility application and the provisional patent application are each by Henry A. Hill and Peter de Groot and the contents both thereof are incorporated herein in their entirety by reference.

A further example of a cyclic error compensation technique is described in commonly owned U.S. Provisional Patent Application No. 60/314,490 and corresponding utility application Ser. No. 10/218,968 entitled "TILTED INTERFEROMETER" by Henry A. Hill. The contents of the provisional patent application and the utility application are incorporated herein in their entireties by reference.

Other techniques for cyclic error compensation include those described in U.S. Pat. No. 6,137,574 entitled "SYSTEMS AND METHODS FOR CHARACTERIZING AND CORRECTING CYCLIC ERRORS IN DISTANCE MEASURING AND DISPERSION INTERFEROMETRY;" No. 6,252,668 B1 entitled "SYSTEMS AND METHODS FOR QUANTIFYING NON-LINEARITIES IN INTERFEROMETRY SYSTEMS;" and No. 6,246,481 entitled "SYSTEMS AND METHODS FOR QUANTIFYING NONLINEARITIES IN INTERFEROMETRY SYSTEMS." All three of the cited patents are by Henry A. Hill and the contents thereof of the three cited patents are herein incorporated in their entirety by reference.

Improved statistical accuracy in measured values of SDP is obtained by taking advantage of the relatively low bandwidth of measured values of SDP compared to the bandwidth of the corresponding linear displacement measurements using averaging or low pass filtering.

The effects of offset errors in the measured values of SDP are measured by use of procedures described in referenced U.S. Provisional Patent Application No. 60/644,898 and U.S. patent application Ser. No. 11/112,681. Details for determining surface figure are also described in referenced U.S. Provisional Patent Applications No. 60/517,426, No. 60/534, 481, No. 60/535,078, No. 60/564,448, and No. 60/644,898 and in referenced U.S. patent application Ser. No. 11/112, 681.

Other forms of a plane mirror configurations such as described in an article entitled "Differential interferometer arrangements for distance and angle measurements: Principles, advantages and applications" by C. Zanoni, *VDI Berichte* Nr. 749, pp 93-106 (1989) may be incorporated into disclosed embodiments.

Interferometer 100 introduces a phase shift $\tilde{\phi}_i$ between the measurement and reference beam components of beam corresponding to $x_i'$. Phase shift $\tilde{\phi}_i'$ is related to physical lengths of portions of the measurement paths $x_i'$ according to the formulae $$\tilde{\phi}_i' = 2k(x_i' + Z_i' + \zeta_i'), \; i=0, 1, 2, \text{ and } 3, \quad (7)$$

where $x_i'$ represents the physical length of the of the measurement path i in interferometer 100, wavenumber $k=2\pi/\lambda$, $\lambda$ is the wavelength of the measurement beam, $Z_i'$ is the stationary effect of the gas in the portion of the measurement path, and $\zeta_i'$ is the contribution of gas turbulence in the respective portion of the measurement path. An electrical interference signal is generated by detectors by the detection of mixed output beams. The detectors comprise analyzers to mix polarization components of output beams The stationary effects of the gas flow in Eq. (7) are compensated by signal processing using known/measured properties of the stationary effects such as described herein in Subsection entitled "Compensation for Stationary Effects" and in the referenced U.S. Pat. No. 6,842,256 and patent application Ser. No. 11/112,681. The compensation of stationary or systematic effects may also be done in part by use of a wavelength monitor such as described in commonly owned U.S. Pat. No. 4,685,803 and U.S. Pat. No. 4,733,967. Both of the patents are by G. E. Sommargren and the contents thereof are herein incorporated in their entirety by reference.

The gas turbulence effects and acoustic perturbation effects are described by representing the gas turbulence and acoustic perturbation effects as an ensemble of cells of gas and acoustic perturbations that move and propagate, respectively, through the measurement paths of beams 171, 172, and 173 in interferometer 100. The spatial distribution of cell or perturbation m of refractivity $[n(x,y,z,t)-1]_T$ is represented by a function $f_m(x,y,z,t)$ such that $$\zeta_i' = \int_{x_i'} [n(x_i', y, z, t) - 1]_T dx_i' \quad (8)$$

$$= \int_{x_i'} \left[ \sum_{m=1} f_m(x_i', y, z, t) \right] dx_i'.$$

Representation of the integration over the respective areas of beams 171, 172, and 173 in Eq. (8) is suppressed. Function $f_m(x_i',y,z,t)$ may vary from cell to cell or from perturbation to perturbation. A cell may represent the effect of a non-uniform composition of the gas or the effect of a turbulent eddy.

As noted herein in the Subsection entitled "Dispersion and Non-Dispersion Interferometry" the frequency domains of the gas turbulence effects and acoustic perturbation effects generally fall into two well separated regions. For the turbulence effects, the corresponding frequency domain is determined by the dimensions of the turbulent cells and the speed of the transport of the cells through the measurement beams 171, 172, and 173. For the example of a turbulence generated cell with a characteristic dimension of 0.04 m and an gas flow speed perpendicular to the axes of the measurement beams 171, 172, and 173 of 0.2 m/s, the corresponding frequency is of the order of 5 Hz. The frequency domain of an acoustic perturbation except for the initial acoustic pulse generated by an acceleration of a measurement object will be determined primarily by the normal mode spectrum of a cavity containing the interferometer 100. For the example of interferometer 100 located in a litho tool with characteristic dimensions of 1.5 m, the normal mode spectrum will comprise a fundamental mode with a frequency of approximately 200 Hz and harmonics thereof.

The initial acoustic pulse generated by an acceleration of a measurement object is classified as a stationary effect and compensated in embodiments of the present invention such as described herein in the Subsection entitled "Compensation for Stationary Effects." The treatment of the initial acoustic pulse generated by an acceleration of a measurement object as a stationary effect is in part a consequence of the property that the initial pulse generally propagates parallel to the measurement axes $x_i$, i=1, 2, and 3 and the corresponding SDP value will not exhibit a significant sensitivity.

The phase shifts $\tilde{\phi}_i' + \tilde{\phi}_0'$, i=1, 2, and 3, are derived from electrical interference signals by known techniques used in processing heterodyne signals for phase information. The processing is by either digital or analog signal processes, preferably digital processes, using time-based phase detection such as a digital Hilbert transform phase detector [see section 4.1.1 of "Phase-locked loops: theory, design, and applications" 2nd ed. McGraw-Hill (New York) 1993, by R. E. Best] or sliding window finite Fourier transform (FFT) techniques.

The gas turbulence and acoustic perturbation component $SDP_T$ of SDP is obtained from Eq. (6) as $$SDP_T = \qquad (9)$$
$$-\frac{1}{2}\int_{x_1'}(n-1)_T dx_1' + \frac{(1+\eta)}{2}\int_{x_2'}(n-1)_T dx_2' - \frac{\eta}{2}\int_{x_3'}(n-1)_T dx_3'.$$

The effect of the gas turbulent cells and acoustic perturbations on $SDP_T$ is obtained by combining Eqs. (8) and (9) with the result $$SDP_T = -\frac{1}{2}\int_{x_1'}\left[\sum_{m=1} f_m(x_1', y, z, t)\right]dx_1' + \qquad (10)$$
$$\frac{(1+\eta)}{2}\int_{x_2'}\left[\sum_{m=1} f_m(x_2', y, z, t)\right]dx_2' - \frac{\eta}{2}\int_{x_3'}\left[\sum_{m=1} f_m(x_3', y, z, t)\right]dx_3'$$

The contributions of gas turbulence effects and acoustic perturbations are separated by generating the temporal Fourier transform of $SDP_T$ by for example a FFT and low pass band and high pass filtering or selection of corresponding portions of the temporal Fourier transform. The contributions of gas turbulence effects and acoustic perturbations correspond to the outputs of the low pass band and high pass band filtering or selection, respectively. The upper and lower pass band frequencies of the low pass band and high pass band, respectively, are approximately 100 Hz for an example for a cavity of a litho tool.

Inversion of Gas Turbulence Effects: Spatial Integrations

The gas turbulence effects which correspond to the output of the low pass filtering may be obtained by an inversion procedure by various different techniques. One technique is performed by treating $SDP_T$ in terms of spatial derivatives such as described in referenced U.S. Pat. No. 6,839,141 and U.S. patent application Ser. No. 10/701,759 and Ser. No. 11/413,917. The second technique is performed by working in the frequency domain using Fourier transforms and inverse Fourier transforms.

In the subsequent discussion herein relating to the inversion of $SDP_T$, it is assumed that the gas flow is arranged to be predominately in the z direction and accordingly, the plane of the measurement axes corresponding to $x_1$, $x_2$, and $x_3$ is aligned so as to be coplanar with the z-x plane.

In the first technique performed by treating $SDP_T$ in terms of spatial derivatives, the gas turbulence effects are represented in Eq. (10) by a Taylor series in the z direction about the $x_2'$ axis. The result is $$SDP_T = \qquad (11)$$
$$-\frac{1}{2}\sum_{m=1}\sum_{p=2}\frac{2^p}{p!}[(-b_2)^p + \eta(b_3-b_2)^p]\int_{x_2'}\left\{\frac{\partial^p f_m(x,y,z,t)}{\partial z^p}\right\}dx_2'.$$

Using the relationship between $(b_3-b_2)$ and $b_2$ given by Eq. (5), Eq. (11) is rewritten as $$SDP_T = \qquad (12)$$
$$b_2\sum_{m=1}\sum_{p=2}\frac{(2b_2)^{p-1}}{p!}\left[(-1)^{p-1}-\left(\frac{1}{\eta}\right)^{p-1}\right]\int_{x_2'}\left\{\frac{\partial^p f_m(x,y,z,t)}{\partial z^p}\right\}dx_2'.$$

Eq. (12) next written in terms of the gas turbulence effect $\zeta_i'$ by changing the order of differentiation and integration and using Eq. (8) as $$SDP_T = b_2\sum_{p=2}\frac{(2b_2)^{p-1}}{p!}\left[(-1)^{p-1}-\left(\frac{1}{\eta}\right)^{p-1}\right]\left(\frac{\partial^p \zeta_2'}{\partial z^p}\right). \qquad (13)$$

The first few terms of Eq. (13) are explicitly written out for subsequent use as $$SDP_T = -\frac{1}{2!}\frac{(2b_2)^2}{2}\left(1+\frac{1}{\eta}\right)\left(\frac{\partial^2 \zeta_2'}{\partial z^2}\right) + \qquad (14)$$
$$\frac{1}{3!}\frac{(2b_2)^3}{2}\left(1-\frac{1}{\eta^2}\right)\left(\frac{\partial^3 \zeta_2'}{\partial z^3}\right) - \frac{1}{4!}\frac{(2b_2)^4}{2}\left(1+\frac{1}{\eta^3}\right)\left(\frac{\partial^4 \zeta_2'}{\partial z^4}\right) + \ldots$$

The leading and typically dominant term in the right hand side of Eq. (14) is the second spatial derivative of $\zeta_2'$ for those spatial frequency components of $\zeta_2'$ that have wavelengths $\gg 2b_2$. Also note that the contribution of the third spatial derivative of $\zeta_2$ relative to the second spatial derivative is reduced by the factor $$\frac{\eta-1}{\eta+1}. \qquad (15)$$

For the example of $\eta=6/5$, the factor of Eq. (15) is 1/6.

Other axes such as $x_1'$ or $x_3'$ could have been chosen as the axis about which to expand in a Taylor series the turbulence effects in Eq. (10). Also an axis could have been chosen such that the term corresponding to the third derivative of $\zeta_2$ in Eq. (14) is 0.

Information about the first derivative of the gas turbulence effects is obtained from the integration with respect to time of Eq. (12) multiplied by a weight function W(t) and u where u is a speed selected to minimize the effects of a non-uniform speed profile along the path of $x_2'$ subsequently discussed with respect to Eq. (19). The value of u will in general be a function of time, i.e. u(t), depending on the position and motion of stage 16. Examples of W(t) are an exponential function $e^{-t/T}$ and $$W(t) = \begin{cases} \left(1 + \frac{t}{T}\right)^q, & -T \le t \le 0 \\ 0, & t > 0, t < -T, \end{cases} \quad (16)$$

where time T is a constant and q is a positive constant >0, e.g. 1 or 2. It is assumed that each gas cell m is moving across the plane of the $x_i'$ measurement paths with a velocity component $u_m$ perpendicular to the $x_i'$ measurement paths. With this assumption and using a value of q=1, the respective integration of Eq. (12) yields the result $$\int_{t-T}^{t}\left[1+\left(\frac{t'-t}{T}\right)\right]u(t')SDP_T(t')dt' = \quad (17)$$

$$+b_2\sum_{m=1}\sum_{p=2}\frac{u}{u_m}\frac{(2b_2)^{p-1}}{p!}\left[(-1)^{p-1}-\left(\frac{1}{\eta}\right)^{p-1}\right] \times$$

$$\int_{x_2'}\left\{\frac{\partial^{p-1} f_m(x_2', y, z, t)}{\partial z^{p-1}}\right\}dx_2' +$$

$$b_2\sum_{m=1}\sum_{p=2}\frac{u}{u_m}\frac{(2b_2)^{p-1}}{p!}\left[(-1)^{p-1}-\left(\frac{1}{\eta}\right)^{p-1}\right] \times$$

$$\int_{t-T}^{t}\left(\frac{1}{T}\right)dt'\int_{x_2'}\left\{\frac{\partial^{p-1} f_m(x_2', y, z, t')}{\partial z^{p-1}}\right\}dx_2'.$$

The velocity component or speed $u_m$ in Eq. (17) which is also in general a function of time is next written as $u+(u_m-u)$ with the result $$\int_{t-T}^{t}\left[1+\left(\frac{t'-t}{T}\right)\right]u(t')SDP_T(t')dt' = \quad (18)$$

$$+b_2\sum_{m=1}\sum_{p=2}\frac{(2b_2)^{p-1}}{p!}\left[1-\left(\frac{u_m-u}{u}\right)+\left(\frac{u_m-u}{u}\right)^2+...\right]\times$$

$$\left[(-1)^{p-1}-\left(\frac{1}{\eta}\right)^{p-1}\right]\int_{x_2'}\left\{\frac{\partial^{p-1} f_m(x_2', y, z, t)}{\partial z^{p-1}}\right\}dx_2' +$$

$$b_2\sum_{m=1}\sum_{p=2}\frac{(2b_2)^{p-1}}{p!}\left[1-\left(\frac{u_m-u}{u}\right)+\left(\frac{u_m-u}{u}\right)^2+...\right]\times$$

$$\left[(-1)^{p-1}-\left(\frac{1}{\eta}\right)^{p-1}\right]$$

$$\int_{t-T}^{t}\left(\frac{1}{T}\right)dt'\int_{x_2'}\left\{\frac{\partial^{p-1} f_m(x_2', y, z, t')}{\partial z^{p-1}}\right\}dx_2'.$$

Eq. (18) is next written in terms of the gas turbulence effect $\zeta_i'$ using Eq. (8) to obtain the formula $$\int_{t-T}^{t}\left[1+\left(\frac{t'-t}{T}\right)\right]u(t')SDP_T(t')dt' = \quad (19)$$

$$+b_2\sum_{p=2}\frac{(2b_2)^{p-1}}{p!}\left[(-1)^{p-1}-\left(\frac{1}{\eta}\right)^{p-1}\right]\frac{\partial^{p-1}\zeta_2'}{\partial z^{p-1}} +$$

-continued $$b_2\sum_{m=1}\sum_{p=2}\frac{(2b_2)^{p-1}}{p!}\left[(-1)^{p-1}-\left(\frac{1}{\eta}\right)^{p-1}\right]\times$$

$$\left[-\left(\frac{u_m-u}{u}\right)+\left(\frac{u_m-u}{u}\right)^2+...\right]\frac{\partial^{p-1}}{\partial z^{p-1}}\int_{x_2'} f_m(x_2', y, z, t)dx_2' +$$

$$b_2\sum_{p=2}\frac{(2b_2)^{p-1}}{p!}\left[(-1)^{p-1}-\left(\frac{1}{\eta}\right)^{p-1}\right]\frac{\partial^{p-1}}{\partial z^{p-1}}\int_{t-T}^{t}\zeta_2'dt' +$$

$$b_2\sum_{m=1}\sum_{p=2}\frac{(2b_2)^{p-1}}{p!}\left[(-1)^{p-1}-\left(\frac{1}{\eta}\right)^{p-1}\right]\times$$

$$\left[-\left(\frac{u_m-u}{u}\right)+\left(\frac{u_m-u}{u}\right)^2+...\right]$$

$$\int_{t-T}^{t}\left(\frac{1}{T}\right)dt'\int_{x_2'}\left\{\frac{\partial^{p-1} f_m(x_2', y, z, t')}{\partial z^{p-1}}\right\}dx_2'.$$

There are on the right hand side of Eq. (19) a first and second single series in p and a first and second double series wherein both are in m and p. The first single series in p with the first few terms of the respective series explicitly written out for subsequent use is given by the formula $$b_2\sum_{p=2}\frac{(2b_2)^{p-1}}{p!}\left[(-1)^{p-1}-\left(\frac{1}{\eta}\right)^{p-1}\right]\frac{\partial^{p-1}\zeta_2'}{\partial z^{p-1}} = \quad (20)$$

$$-\frac{1}{2!}\frac{(2b_2)^{p-1}}{2}\left(1+\frac{1}{\eta}\right)\left(\frac{\partial\zeta_2'}{\partial z}\right)+\frac{1}{3!}\frac{(2b_2)^3}{2}\left(1-\frac{1}{\eta^2}\right)\left(\frac{\partial^2\zeta_2'}{\partial z^2}\right)-$$

$$\frac{1}{4!}\frac{(2b_2)^4}{2}\left(1+\frac{1}{\eta^3}\right)\left(\frac{\partial^3\zeta_2'}{\partial z^3}\right)+....$$

The leading and typically dominant term in the right hand side of Eq. (20) is the first spatial derivative of $\zeta_2'$ for those spatial frequency components of $\zeta_2'$ that have wavelengths $>>2b_2$. Also note that the contribution of the second spatial derivative of $\zeta_2$ relative to the first spatial derivative is reduced by the factor given by Eq. (15).

The second single series in p represents spatial derivatives of the temporal average of $\zeta_2$ over period T. Thus the average value of the second single series in p is 0 and has a variance that is reduced by the number of statistically independent values of $\zeta_2$ that exist for the measurement beam paths in period T. The number will be a function of the characteristic size of the turbulence cells, i.e. the variance will be reduced by a factor proportional to the characteristic size of the turbulence cells. For example, for cells with a characteristic size of 2 cm, T=2 sec, and $u_m$=50 cm/sec, the number is ≅50 or the corresponding statistical error is reduced by a factor of $50^{1/2} \cong 7$.

The magnitude of the first double series in m and p in Eq. (19) is reduced as a consequence of only the deviation of $u_m$ from u appears as a factor. In particular, the magnitude of the first double series in m and p can be used to define the best value to use for u(t), e.g., the value of u(t) is chosen such that the standard deviation of the magnitude of the first double series in m and p is a minimum. With the first order term in $(u_m-u)/u$ eliminated statistically, the largest term remaining will generally be the second order term in $(u_m-u)/u$, i.e. $[(u_m-u)/u]^2$. This greatly reduces sensitivity to variations of $u_m$ along the measurement path $x_2'$. Consider for example the case where the distribution function of $(u_m-u)/u$ is a rectangle function $0.6 \leq u_m/u \leq 1.4$. The respective average value $\langle [(u_m-u)/u]^2 \rangle$ of $[(u_m-u)/u]^2$ is $$\langle [(u_m - u)/u]^2 \rangle \cong \frac{(0.4)^2}{3} \cong 0.05. \tag{21}$$

The magnitude of the second double series in m and p in Eq. (19) is reduced as a consequence of the two properties and the elimination of terms that are first order in $(u_m-u)/u$ and therefore reduced to a second order effect. The two properties are the effects of temporal averaging $\zeta_2$ of discussed with respect to the second single series p and the effects of only the deviation of $u_m$ from a u appears as a factor leading to the elimination of terms that are first order in $(u_m-u)/u$ such as discussed with respect to the first double series in m and p.

Thus the first spatial derivative of $\eta_2'$ for those spatial frequency components of $\zeta_2'$ that have wavelengths $>>2b_2$ is the leading dominant term on the right side of Eq. (19) as well as the right hand side of Eq. (20). The first few terms of Eq. (19) are explicitly written out for subsequent use as $$\int_{t-T}^{t} \left[1 + \left(\frac{t'-t}{T}\right)\right] u(t') SDP_T(t') dt' = -\frac{1}{2!}\frac{(2b_2)^2}{2}\left(1+\frac{1}{\eta}\right)\left(\frac{\partial \zeta_2'}{\partial z}\right) + \tag{22}$$

$$\frac{1}{3!}\frac{(2b_2)^3}{2}\left(1-\frac{1}{\eta^2}\right)\left(\frac{\partial^2 \zeta_2'}{\partial z^2}\right) - \frac{1}{4!}\frac{(2b_2)^4}{2}\left(1+\frac{1}{\eta^3}\right)\left(\frac{\partial^3 \zeta_2'}{\partial z^3}\right) + \ldots$$

Information about the atmospheric turbulence effect $\zeta_2'(t)$ on the optical path length of path $x_2'$ is obtained from the derived value of first spatial derivative of the gas turbulence effects given by Eqs. (19) and (20) by the same procedure that was described for obtaining information about the of first spatial derivative of the gas turbulence effects from the second spatial derivative of the gas turbulence effects. The result is given by the following formula $$\int_{t-T}^{t} \left[1+\left(\frac{t'-t}{T}\right)\right] u(t') dt' \int_{t'-T}^{t'} \left[1+\left(\frac{t''-t'}{T}\right)\right] u(t'') SDP_T(t'') dt'' = \tag{23}$$

$$+b_2 \sum_{p=2} \frac{(2b_2)^{p-1}}{p!}\left[(-1)^{p-1}-\left(\frac{1}{\eta}\right)^{p-1}\right]\frac{\partial^{p-2} \zeta_2'}{\partial z^{p-2}} +$$

$$b_2 \sum_{m=1} \sum_{p=2} \frac{(2b_2)^{p-1}}{p!}\left[(-1)^{p-1}-\left(\frac{1}{\eta}\right)^{p-1}\right] \times$$

$$\left[-\left(\frac{u_m-u}{u}\right)+\left(\frac{u_m-u}{u}\right)^2+\ldots\right]\frac{\partial^{p-2}}{\partial z^{p-2}}\int_{x_2'} f_m(x_2',y,z,t) dx_2' +$$

$$b_2 \sum_{p=2} \frac{(2b_2)^{p-1}}{p!}\left[(-1)^{p-1}-\right.$$

$$\left.\left(\frac{1}{\eta}\right)^{p-1}\right]\frac{\partial^{p-2}}{\partial z^{p-2}}\int_{t-T}^{t}\left(\frac{1}{T}\right)dt'\int_{t'-T}^{t'} \zeta_2' dt'' + \ldots$$

The first few terms of Eq. (23) are explicitly written out for sub sequent use as $$\int_{t-T}^{t}\left[1+\left(\frac{t'-t}{T}\right)\right]u(t')dt'\int_{t'-T}^{t'}\left[1+\left(\frac{t''-t'}{T}\right)\right]u(t'')SDP_T(t'')dt'' = \tag{24}$$

$$-\frac{1}{2!}\frac{(2b_2)^2}{2}\left(1+\frac{1}{\eta}\right)\zeta_2' + \frac{1}{3!}\frac{(2b_2)^3}{2}\left(1-\frac{1}{\eta^2}\right)\left(\frac{\partial^2 \zeta_2}{\partial z}\right) -$$

$$\frac{1}{4!}\frac{(2b_2)^4}{2}\left(1+\frac{1}{\eta^3}\right)\left(\frac{\partial \zeta_2'}{\partial z^2}\right) + \ldots.$$

The omitted terms in Eq. (24) are reduced by first and higher effects such as described in relation to the reduction of the magnitudes of terms in Eq. (19) due to time averaging and the $(u_m-u)/u$ factor.

Values of $\zeta_2'(t)$, $\partial \zeta_2'(t)/\partial z$, and $\partial^2 \zeta_2'(t)/\partial z^2$ are obtained from combinations of Eqs. (14), (22), and (24) and subsequently used to correct for the effects of gas turbulence in measurement path $x_i'$, $i=0, 1, 2, 3$, or some other path displaced from $x_2'$.

Inversion of Gas Turbulence and Acoustic Perturbation Effects: Fourier Transform Inversion Techniques The second difference parameter given by Eq. (9) can be written in terms of the acoustic perturbation or turbulence effect $\zeta_i'$, $i=1, 2$, and 3 as $$SDP_T = -\frac{1}{2}\zeta_1'(t) + \frac{(1+\eta)}{2}\zeta_2'(t) - \frac{\eta}{2}\zeta_3'(t). \tag{25}$$

Acoustic perturbation or turbulence effects $\zeta_i'$, $i=1, 2$, and 3 are related by simple time delays $\tau$ and $\tau/\eta$ as expressed in the following formula $$SDP_T = -\frac{1}{2}\zeta_2'(t-\tau) + \frac{(1+\eta)}{2}\zeta_2'(t) - \frac{\eta}{2}\zeta_2'\left(t+\frac{\tau}{\eta}\right) \tag{26}$$

where $\tau$ is equal to $\tau_A$ and $\tau_T$ for an acoustic perturbation effect and turbulence effect, respectively.

The Fourier transform of Eq. (26) is next written the following form using the translation properties of a Fourier transform with the result $$F(SDP_T) = \left[-\frac{1}{2}e^{i\omega\tau} + \frac{(1+\eta)}{2} - \frac{\eta}{2}e^{-i(\omega\tau/\eta)}\right]F[\zeta_2'(t)]. \tag{27}$$

The average of the Fourier transform given by Eq. (27) is next performed over an array of $\tau$ values present at frequency $\omega$. The result of the averaging is the equation $$\langle F(SDP_T) \rangle = \left[-\left\langle\frac{1}{2}e^{i\omega\tau}\right\rangle + \frac{(1+\eta)}{2} - \frac{\eta}{2}\langle e^{-i(\omega\tau/\eta)}\rangle\right]F[\zeta_2'(t)] \tag{28}$$

For acoustic perturbations where the distribution of directions of acoustic perturbations is on the average axially symmetric with respect to the measurement axis $x_2'$, the effect of the average over the array of $\tau$ values for certain terms in Eq. (28) can be written in the form $$\langle e^{i\omega\tau}\rangle = \langle \cos(\omega\tau_A)\rangle$$

$$\langle e^{-i(\omega\tau)/\eta}\rangle = \langle \cos[(\omega\tau_A)/\eta]\rangle \tag{29}$$

For turbulence effects, the average over the array of $\tau$ values of the certain terms in Eq. (28) will in general retain a complex component. The factor multiplying the Fourier transform $F[\zeta_2'(t)]$ on the right hand side of Eq. (28) is expressed in a reduced form for axially symmetric acoustic perturbations using the equations of Eqs. (29) as $$\left[-\left\langle \frac{1}{2}e^{i\omega\tau}\right\rangle + \frac{(1+\eta)}{2} - \frac{\eta}{2}\langle e^{-i(\omega\tau/\eta)}\rangle\right] = \qquad (30)$$
$$+ \frac{1}{2}[1 - \langle\cos\omega\tau_A\rangle] + \frac{\eta}{2}[1 - \langle\cos(\omega\tau_A/\eta)\rangle] = +$$
$$[\langle\sin^2(\omega\tau_A/2)\rangle + \eta\langle\sin^2(\omega\tau_A/2\eta)\rangle]$$

where $$\tau_A = \frac{\cos\psi}{\sin\gamma}\left(\frac{2b_2}{u_s}\right), \qquad (31)$$

$u_s$ is the speed of sound, $\gamma$ is the angle between the direction of propagation of the acoustic perturbation and the direction of measurement axis $x_2'$, and $\psi$ is the azimuthal angle of the direction of propagation of the acoustic perturbation relative to the plane defined by the three axes of the multi-axis interferometer. The average values of terms in Eq. (28) represent the average over angles $\gamma$ and $\psi$. For those end use applications where the distribution of directions of acoustic perturbations is on the average not axially symmetric with respect to the measurement axis $x_2'$, Eq. (28) is used in subsequent steps in the inversion of $SDP_T$.

The value $\tau_T$ that is used for $\tau$ in Eq. (28) for addressing turbulence effects can be expressed as $$\tau_T = \frac{\cos\psi}{\sin\gamma}\left(\frac{2b_2}{u_T}\right), \qquad (32)$$

where $u_T$ is an average value of the speed of the air flow at the measurement path $x_2'$, $\gamma$ is the angle between the direction of flow of the air and the direction of measurement axis $x_2'$, and $\psi$ is the azimuthal angle of the direction of flow of the air relative to the plane defined by the three axes of the multi-axis interferometer. The average value $u_t$ which represents the average with respect to position along measurement path $x_2'$ will be a function of time and the values of $u_T$ are selected so as to minimize the residual errors left after a compensation for effects of turbulence effects is made. The description of the basis for the selection of values of $u_T$ is the same as the description given for the selection of values for u herein in the Subsection entitled "Inversion of Gas Turbulence Effects: Spatial Integrations" [in particular, see the discussion herein that precedes Eq. (21)

The Fourier transform $F[\zeta_2'(t)]$ for the respective frequency domains for acoustic perturbation and turbulence effects is obtained from Eq. (28) to obtain with the use of Eq. (30) the result $$F[\zeta_2'(t)] = \left[-\left\langle \frac{1}{2}e^{i\omega\tau}\right\rangle + \frac{(1+\eta)}{2} - \frac{\eta}{2}\langle e^{-i(\omega\tau/\eta)}\rangle\right]^{-1}\langle F(SDP_T)\rangle. \qquad (33)$$

The inverse Fourier transform $[\zeta_2'(t)]_I$ of $F[\zeta_2'(t)]$ is computed to obtain the acoustic perturbation or air turbulence effect in a respective frequency band centered at frequency $\omega$ with the result $$[\zeta_2'(t)]_I = F^{-1}\left\{\left[-\left\langle \frac{1}{2}e^{i\omega\tau}\right\rangle + \frac{(1+\eta)}{2} - \frac{\eta}{2}\langle e^{-i(\omega\tau/\eta)}\rangle\right]^{-1}\langle F(SDP_T)\rangle\right\} \qquad (34)$$

where $F^{-1}(g)$ is the inverse Fourier transform of function g.

Inverse Fourier transform $[\zeta_2'(t)]_I$ includes a constant term and a linear term corresponding to the constants of integration discussed in the Subsection herein entitled "Inversion of Gas Turbulence Effects: Spatial Integrations." The constant and linear terms can be eliminated subsequently by subtracting the average value of $[\zeta_2'(t)]_I$ from the value of $[\zeta_2'(t)]_I$ at the end point of interest.

Another technique for inversion of gas turbulence and acoustic perturbations is based on application of Fourier series techniques. For a time period covering a time domain T, acoustic perturbation or turbulence effect $\zeta_i'$ is expressed by the Fourier series $$\zeta'(t) = \sum_{m=1}^{N} A_m \cos\left[m2\pi\frac{(t-\bar{t})}{T}\right] + \sum_{m=1}^{N} B_m \sin\left[m2\pi\frac{(t-\bar{t})}{T}\right], \qquad (35)$$
$$-\frac{1}{2} \le \frac{(t-\bar{t})}{T} \le \frac{1}{2},$$

where $\tau$ can in general will be a function of time, $\bar{t}$ is the average value of time t over the time domain (t−T) to t, and N is an integer determined by consideration of the temporal frequencies that are to be included in the series representation. A constant value is omitted from Eq. (35) since the average value of $\zeta_i'$ should statistically be zero.

Using the definition of SDP given by Eq. (26), the corresponding series for SDP is next written as $$SDP(t) = \frac{1}{2}\sum_{m=1}^{N} \cos\left[m2\pi\frac{(t-\bar{t})}{T}\right] \times \qquad (36)$$
$$\left\{\begin{array}{l}A_m\left[(1+\eta) - \cos\left(m2\pi\frac{\tau}{T}\right) - \eta\cos\left(m2\pi\frac{\tau}{\eta T}\right)\right] \\ +B_m\left[\sin\left(m2\pi\frac{\tau}{T}\right) - \eta\sin\left(m2\pi\frac{\tau}{\eta T}\right)\right]\end{array}\right\} +$$
$$\frac{1}{2}\sum_{m=1}^{N} \sin\left[m2\pi\frac{(t-\bar{t})}{T}\right] \times$$
$$\left\{\begin{array}{l}-A_m\left[\sin\left(m2\pi\frac{\tau}{T}\right) - \eta\sin\left(m2\pi\frac{\tau}{\eta T}\right)\right] \\ +B_m\left[(1+\eta) - \cos\left(m2\pi\frac{\tau}{T}\right) - \eta\cos\left(m2\pi\frac{\tau}{\eta T}\right)\right]\end{array}\right\},$$
$$-\frac{1}{2} \le \frac{(t-\bar{t})}{T} \le \frac{1}{2},$$

A contracted form of Eq. (36) is obtained with the introduction of $A_m'$ and $B_m'$ as $$SDP(t) = \frac{1}{2}\sum_{m=1}^{N}\left[\cos\left[m2\pi\frac{(t-\bar{t})}{T}\right]A'_m + \sin\left[m2\pi\frac{(t-\bar{t})}{T}\right]B'_m\right], \quad (37)$$

$$-\frac{1}{2} \leq \frac{(t-\bar{t})}{T} \leq \frac{1}{2}$$

where $$A'_m = \int_{\frac{(t'-\bar{t})}{T}=-\frac{1}{2}}^{\frac{(t'-\bar{t})}{T}=\frac{1}{2}} \frac{1}{T} SDP(t')\cos\left[m2\pi\frac{(t'-\bar{t})}{T}\right]dt', \, m > 0; \quad (38)$$

$$B'_m = \int_{\frac{(t'-\bar{t})}{T}=-\frac{1}{2}}^{\frac{(t'-\bar{t})}{T}=\frac{1}{2}} \frac{1}{T} SDP(t')\sin\left[m2\pi\frac{(t'-\bar{t})}{T}\right]dt', \, m > 0. \quad (39)$$

With the expressions for SDP(t) given by Eqs. (36) and (37), equations for $A_m'$ and $B_m'$ can be written in terms of $A_m$ and $B_m$ as $$A'_p = \int_{\frac{(t-\bar{t})}{T} \geq -\frac{1}{2}}^{\frac{(t-\bar{t})}{T} \leq \frac{1}{2}} \cos\left[p2\pi\frac{(t-\bar{t})}{T}\right]\sum_{m=1}^{N}\cos\left[m2\pi\frac{(t-\bar{t})}{T}\right] \times \quad (40)$$

$$\begin{Bmatrix} A_m\left[(1+\eta) - \cos\left(m2\pi\frac{\tau}{T}\right) - \eta\cos\left(m2\pi\frac{\tau}{\eta T}\right)\right] \\ +B_m\left[\sin\left(m2\pi\frac{\tau}{T}\right) - \eta\sin\left(m2\pi\frac{\tau}{\eta T}\right)\right] \end{Bmatrix} dt +$$

$$\int_{\frac{(t-\bar{t})}{T} \geq -\frac{1}{2}}^{\frac{(t-\bar{t})}{T} \leq \frac{1}{2}} \cos\left[p2\pi\frac{(t-\bar{t})}{T}\right]\sum_{m=1}^{N}\sin\left[m2\pi\frac{(t-\bar{t})}{T}\right] \times$$

$$\begin{Bmatrix} -A_m\left[\sin\left(m2\pi\frac{\tau}{T}\right) - \eta\sin\left(m2\pi\frac{\tau}{\eta T}\right)\right] \\ +B_m\left[(1+\eta) - \cos\left(m2\pi\frac{\tau}{T}\right) - \eta\cos\left(m2\pi\frac{\tau}{\eta T}\right)\right] \end{Bmatrix} dt, \, p > 0,$$

$$B'_p = \int_{\frac{(t-\bar{t})}{T} \geq -\frac{1}{2}}^{\frac{(t-\bar{t})}{T} \leq \frac{1}{2}} \sin\left[p2\pi\frac{(t-\bar{t})}{T}\right]\sum_{m=1}^{N}\cos\left[m2\pi\frac{(t-\bar{t})}{T}\right] \times \quad (41)$$

$$\begin{Bmatrix} A_m\left[(1+\eta) - \cos\left(m2\pi\frac{\tau}{T}\right) - \eta\cos\left(m2\pi\frac{\tau}{\eta T}\right)\right] \\ +B_m\left[\sin\left(m2\pi\frac{\tau}{T}\right) - \eta\sin\left(m2\pi\frac{\tau}{\eta T}\right)\right] \end{Bmatrix} dt +$$

$$\int_{\frac{(t-\bar{t})}{T} \geq -\frac{1}{2}}^{\frac{(t-\bar{t})}{T} \leq \frac{1}{2}} \sin\left[p2\pi\frac{(t-\bar{t})}{T}\right]\sum_{m=1}^{N}\sin\left[m2\pi\frac{(t-\bar{t})}{T}\right] \times$$

$$\begin{Bmatrix} -A_m\left[\sin\left(m2\pi\frac{\tau}{T}\right) - \eta\sin\left(m2\pi\frac{\tau}{\eta T}\right)\right] \\ +B_m\left[(1+\eta) - \cos\left(m2\pi\frac{\tau}{T}\right) - \eta\cos\left(m2\pi\frac{\tau}{\eta T}\right)\right] \end{Bmatrix} dt, \, p > 0.$$

Eqs. (40) and (41) can be written in the contracted matrix form $$\begin{pmatrix} A'_1 \\ \vdots \\ A'_N \\ B'_1 \\ \vdots \\ B'_N \end{pmatrix} = (M_{n,m}) \begin{pmatrix} A_1 \\ \vdots \\ A_N \\ B_1 \\ \vdots \\ B_N \end{pmatrix} \quad (42)$$

where the matrix elements $M_{n,m}$ of matrix $(M_{n,m})$ are given by corresponding factors in Eqs. (40) and (41).

For the situation where the deviation of $\tau$ from an average value $\bar{\tau}$ is a small fraction of $\bar{\tau}$, i.e., $|\tau-\bar{\tau}|/\bar{\tau} \ll 1$, the off diagonal matrix elements of matrix $(M_{n,m})$ are in general small compared to the corresponding diagonal matrix elements. In the case where the off diagonal matrix elements can be neglected, the matrix transformation expressed by Eq. (42) can be written in another contracted form where $A_p'$ and $B_p'$ are obtained from $A_p'$ and $B_p'$ by a complex rotation operator T. Complex rotation or transfer operator T has real and imaginary components $Re(T_p)$ and $Im(T_p)$ where $$A_p' = |T_p|[A_p \cos\theta + B_p \sin\theta], \quad (43)$$

$$B_p' = |T_p|[-A_p \sin\theta + B_p \cos\theta], \quad (44)$$

$$\tan\vartheta = \frac{Im(T_p)}{Re(T_p)}. \quad (45)$$

The real and imaginary components $Re(T_p)$ and $Im(T_p)$ are given by the formulae $$Re(T_p) = \left[(1+\eta) - \cos\left(p2\pi\frac{\tau}{T}\right) - \eta\cos\left(p2\pi\frac{\tau}{\eta T}\right)\right], \, p > 0, \quad (46)$$

$$Im(T_p) = \left[\sin\left(p2\pi\frac{\tau}{T}\right) - \eta\sin\left(p2\pi\frac{\tau}{\eta T}\right)\right], \, p > 0. \quad (47)$$

Figure 6:
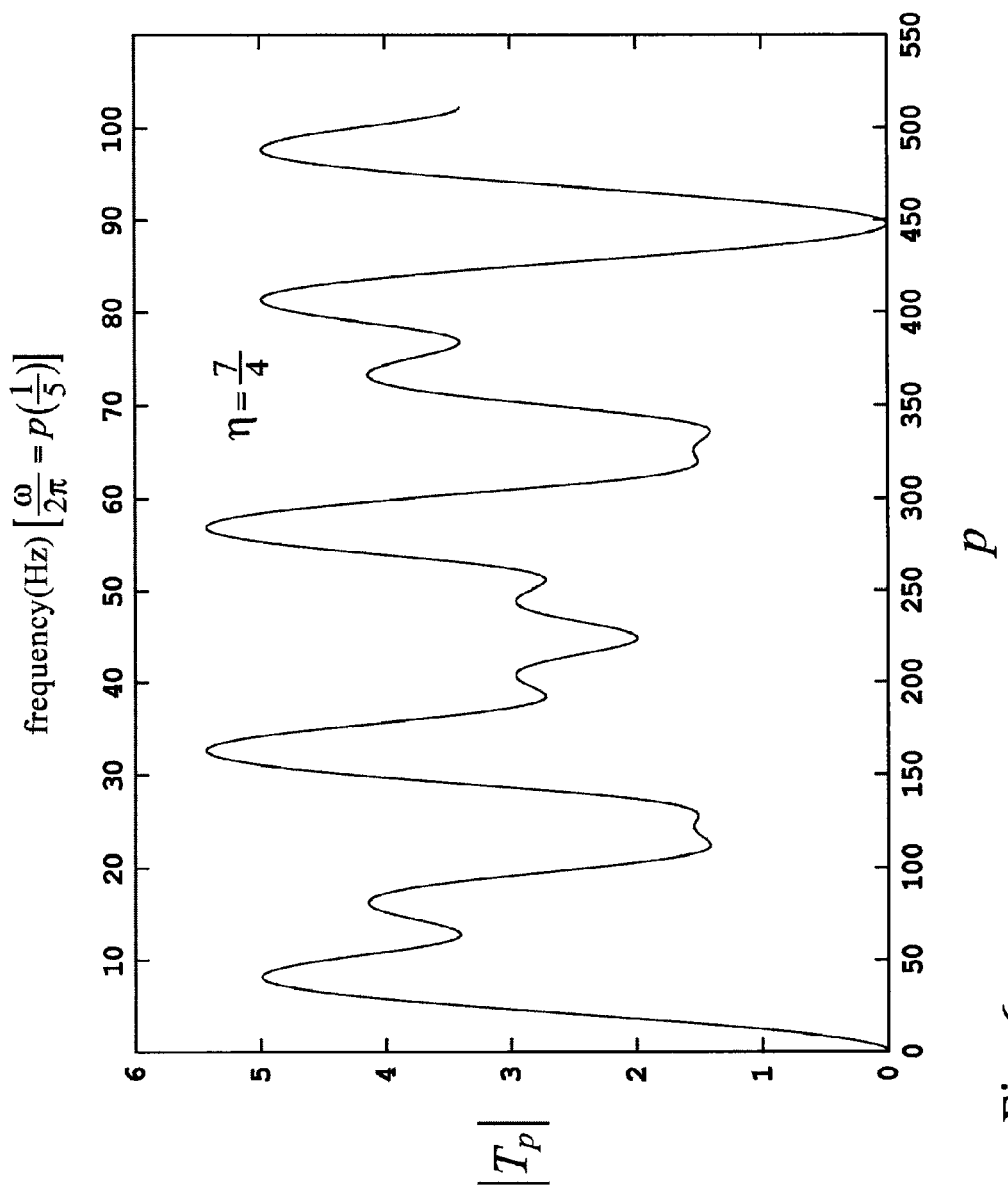
FIG. 6 is a graphical representation of the properties of the magnitude of the transfer properties of SDP in an embodiment.

As an example, the magnitude $|T_p|$ of $T_p$ is plotted in FIG. 6 as a function of p for T=5 sec, $\tau$=0.0781 sec, and $\eta$=7/4. The scale at the top of FIG. 6 is the frequency $\omega/2\pi$=p(1/T). The first zero in $|T_p|$ beyond the zero at p=0 occurs at p=448. The frequency $\omega/2\pi$=p(1/T) is 89.6 Hz. at p=448 which is located in between typical values of frequency domains of the turbulence and acoustic perturbation effects. The actual location of the first zero in $|T_p|$ beyond the zero at p=0 is selected by design of the beam spacings for a given gas flow pattern based on consideration of the relative locations of frequency domains of the turbulence and acoustic perturbation effects.

Elimination of Effects of Gibbs Phenomenon

The effects of the Gibbs phenomenon associated with discontinuity when using a Fourier series representation [see, e.g., Section 14.5 entitled "Gibbs Phenomenon" in the book by G. Arfken *Mathematical Methods For Physicists*, Academic Press (1966)], are eliminated in embodiments of the present invention by the addition of a polynomial to the measured values of SDP. The polynomial is selected to remove any discontinuity that may occur in the measured values of SDP at the limits of the time domain $-1/2 \leq (t-\bar{t})/T \leq 1/2$ and for which the inversion is easily obtained. For the function $$g(t) = \frac{1}{3!}D(t-\bar{t})^3 + \frac{1}{4!}E(t-\bar{t})^4 \quad (48)$$

where D and E are constants, the SDP(g) is $$SDP(g) = -\frac{D}{3!}\frac{\tau^2}{2}\left[3(t-\bar{t})\left(1+\frac{1}{\eta}\right) - \tau\left(1-\frac{1}{\eta^2}\right)\right] - \quad (49)$$

$$\frac{E}{4!}\frac{\tau^2}{2}\left[6(t-\bar{t})^2\left(1+\frac{1}{\eta}\right) - 4\tau(t-\bar{t})\left(1-\frac{1}{\eta^2}\right) + \tau^2\left(1+\frac{1}{\eta^3}\right)\right].$$

The values of the constants D and E are selected the values of $[SDP(\zeta_i')+SDP(g)]$ are zero at the limits of the time domain $-1/2 \leq (t-\bar{t})/T \leq 1/2$ where $SDP(\zeta_i')$ corresponds to the contribution from turbulence and acoustic perturbation effects. This is easily done by working with the measured values of SDP $(\zeta_i')$ and the corresponding temporal derivatives at the limits of the time domain $-1/2 \leq (t-\bar{t})/T \leq 1/2$. The value of the respective function g(t) is subtracted from the function obtained from the inversion of $[SDP(\zeta_i')+SDP(g)]$ using the Fourier series techniques described herein to obtain $\zeta_i'$.

Higher order polynomials may also be used for function g(t). In addition, if only the effects of one discontinuity in $SDP(\zeta_i')$ need be eliminated, the value of constant E can be set equal to zero.

Compensation for Stationary Effects

Also, SDP parameters may be used in a procedure for a non-dispersive compensation for stationary non-random systematic effects in the refractivity of gas in the measurement and/or reference beam paths. Non-random changes (i.e., systematic changes) in refractivity include effects of changes in gas density and composition. As used herein, the property of stationarity means that the probability-space parameters of a process classified as stationary are invariant under a translation in time modulo a time interval. In other words, the mean and variance of the relevant probability-space parameters are related at equivalent stages of each exposure cycle of a lithography tool. The aforementioned time interval for a given lithography tool is the reciprocal of the rate at which wafers are processed by the tool. The description of the treatment of the stationary non-random systematic effects in relation to the surface figure error function of a stage mirror can be the same as the corresponding description in U.S. Pat. No. 6,842,256, the entire contents of which is hereby incorporated by reference. For example, the system can include a refractometer that measures the refractivity of the atmosphere at some location remote from the measurement beams, but at a location where the refractivity of the atmosphere is related to the refractivity in the measurement beam paths (e.g., at a location within a chamber housing the interferometers and measurement objects, such as in a lithography tool chamber). Measurements made using the interferometers can be corrected based on the refractivity measurements using a non-trivial function (e.g., more complex than a one-to-one correspondence) that maps the gas refractivity at the measurement beam path to a remote location where the refractivity is measured based on the system conditions at the time the refractivity was made.

Combination of Dispersion and Non-Dispersion Interferometry Techniques

Embodiments can include a combination of both dispersion and non-dispersion interferometry techniques for those end use applications wherein one of the two techniques of dispersion and non-dispersion interferometry does not achieve a desired level of compensation and it is desired to use that one of the two techniques. The description of the non-dispersion interferometry techniques used in the combination is the same as the corresponding portions of descriptions given herein that feature non-dispersion interferometry techniques.

Dispersive interferometry techniques detect the effects of a fluctuating refractive index over a measurement path by making a distance measurement multiple-wavelength. The basic principle may be understood as follows. Interferometers and laser radar measure the optical path length between a reference and an object, most often in open air. The optical path length is the integrated product of the refractive index and the physical path traversed by a measurement beam. In that the refractive index varies with wavelength, but the physical path is independent of wavelength, it is generally possible to determine the physical path length from the optical path length, particularly the contributions of fluctuations in refractive index, provided that the instrument employs at least two wavelengths.

An example of a two wavelength interferometry system for microlithography is represented by U.S. Pat. No. 4,948,254 issued to A. Ishida (1990). A similar device is described by Ishida in an article entitled "Two Wavelength Displacement-Measuring Interferometer Using Second-Harmonic Light To Eliminate Air-Turbulence-Induced Errors," Jpn. J. Appl. Phys. 28(3), L473-475 (1989). In the article, a displacement-measuring interferometer is disclosed which eliminates errors caused by fluctuations in the refractive index by means of two-wavelength dispersion detection. An Ar+ laser source provides both wavelengths simultaneously by means of a frequency-doubling crystal known in the art as BBO. The use of a BBO doubling crystal results in two wavelengths that are fundamentally phase locked, thus greatly improving the stability and accuracy of the refractive index measurement.

In U.S. Pat. No. 5,404,222 entitled "INTERFEROMETRIC MEASURING SYSTEM WITH AIR TURBULENCE COMPENSATION," issued to S. A. Lis (1995), there is disclosed a two-wavelength interferometer employing the dispersion technique for detecting and compensating refractive index fluctuations. A similar device is described by Lis in an article entitled "An Air Turbulence Compensated Interferometer For IC Manufacturing," SPIE 2440 (1995). Improvement on U.S. Pat. No. 5,404,222 by S. A. Lis is disclosed in U.S. Pat. No. 5,537,209. The principal innovation of this system with respect to that taught by Ishida in Jpn. J. Appl. Phys. (supra) is the addition of a second BBO doubling crystal to improve the precision of the phase detection means. The additional BBO crystal makes it possible to optically interfere two beams having wavelengths that are exactly a factor of two different. The resultant interference has a phase that is directly dependent on the refractive index but is substantially independent of stage motion.

Two two-wavelength distance measuring systems based on superheterodyne techniques are described in commonly owned U.S. Pat. No. 5,764,362 entitled "SUPERHETERODYNE METHOD AND APPARATUS FOR MEASURING THE REFRACTIVE INDEX OF AIR USING MULTIPLE-PASS INTERFEROMETRY" by Henry A. Hill and P. de Groot and U.S. Pat. No. 5,838,485 entitled "SUPERHETERODYNE INTERFEROMETER AND METHODS FOR COMPENSATING THE REFRACTIVE INDEX OF AIR USING ELECTRONIC FREQUENCY MULTIPLICATION" by Peter de Groot and Henry A. Hill. The contents of both of the two cited patents are herein incorporated in their entirety by reference. In both of the two referenced patents, contributions to measured phases due to effects of a gas in a measurement path are directly dependent on the refractive index but the contributions due to stage motion are substantially reduced. The first of the two referenced patents is based on multiple pass interferometry and the second referenced patent is based on electronic frequency multiplication.

Dispersion interferometry techniques typically include monitoring wavelength and/or monitoring an intrinsic property of the gas (e.g., reciprocal dispersive power). A commonly owned U.S. patent relating to the measurement of intrinsic properties of a gas such as the reciprocal dispersive power is U.S. Pat. No. 6,124,931. The contents of the commonly owned cited patent is herein incorporated in their entirety by reference.

Embodiments can include the dispersion interferometry techniques including the description of wavelength monitors and monitors of the reciprocal dispersive power of a gas are the same as the corresponding portions of descriptions given in referenced U.S. Pat. No. 5,764,362, U.S. Pat. No. 5,838, 485, U.S. Pat. No. 6,330,065 B1, U.S. Pat. No. 6,124,931, U.S. Pat. No. 6,327,039 B1, U.S. Pat. No. 6,407,866, U.S. Pat. No. 6,525,825, U.S. Pat. No. 6,525,826 B2, U.S. Pat. No. 6,529,279, and U.S. Pat. No. 6,219,144 B1, the entire contents all of which are hereby incorporated by reference.

Additional Embodiments

Furthermore, while the foregoing description relates to determining and compensating for variations in the optical properties of a gas in the measurement beams of an interferometer, the techniques described herein can be applied to the interferometer reference beams in addition, or alternatively, to the measurement beams. For example, in systems where there is gas in the reference beam paths, such as where the system uses a column reference, information about variations in the optical properties of that gas can be determined along with the information about the variations in the optical properties of the gas in the measurement beam paths.

Moreover, while the foregoing description details determining and compensating for variations in the optical properties of a gas due to turbulence for gas flow in one direction, in general, the system can be configured to implement these methods to determine information about gas turbulence for more than one gas flow direction. For example, system 15 (FIG. 1a) can be configured to determine information about gas turbulence from both 3 axes/plane interferometers 10 and 20, providing information about turbulence in two orthogonal gas flow directions. More generally, systems can be configured to include more than two 3 axes/plane interferometers for determining information about gas turbulence in more than two gas flow directions. The directions need not be orthogonal.

Moreover, systems can be configured to determine gas turbulence information for more than one location in a system. For example, as in system 15, different 3 axes/plane interferometers can be positioned on adjacent sides of a moveable stage, providing gas turbulence information at those locations. Alternatively, or additionally, a second 3 axes/plane interferometer can be provided on the same side of the system as interferometer 10, oriented with its measurement axes parallel to but in an orthogonal plane to the plane in which the measurement axes of interferometer 10 lie. Accordingly, the system can determine information about turbulence effects flowing in orthogonal directions between interferometer 10 and stage 16. Of course, other configurations are also possible.

In general, any of the analysis methods described above can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis methods can also be implemented as a computer-readable storage medium, configured with a computer program, where the storage medium so configured causes a computer to operate in a specific and predefined manner to perform the functions described herein.

In embodiments, various other error compensation techniques can be used to reduce other sources of error in interferometer measurements. For example, stationary effects of the gas flow in Equation (8) can be compensated by signal processing using known/measured properties of the stationary effects such as described in the cited U.S. Pat. No. 6,842, 256 and U.S. Pub. No. 2005 0237536 A1. The compensation of stationary or systematic effects may also be done in part by use of a wavelength monitor such as described in commonly owned U.S. Pat. No. 4,685,803 and No. 4,733,967. Both of the patents are by G. E. Sommargren and the contents thereof are herein incorporated in their entirety by reference.

In some embodiments, the effects of offset errors in the measured values of SDP can be measured by use of procedures described in U.S. Pub. No.'s US 2005 0248772 A1 and 2005 0237536 A1. Details for determining surface figure are also described in U.S. Pub. No. 2005 0162664 A1 and U.S. Pub. No. 2005-0146727 A1. The contents of the four aforementioned publications are all hereby incorporated by reference in their entirety.

In certain embodiments, cyclic errors in interferometer measurements can also be compensated. Cyclic errors that are present in the linear displacement measurements can be reduced (e.g., eliminated) and/or compensated by use of one of more techniques such as described in U.S. Pat. No. 6,891, 624, entitled "CYCLIC ERROR REDUCTION IN AVERAGE INTERFEROMETRIC MEASUREMENTS," and U.S. Pat. No. 6,950,192, entitled "CYCLIC ERROR COMPENSATION IN INTERFEROMETRY SYSTEMS," both of which are by Henry A. Hill and the contents of which are incorporated herein in their entirety by reference.

An example of another cyclic error compensation technique is described in commonly owned U.S. Pat. No. 6,806, 961, entitled "INTERFEROMETRIC CYCLIC ERROR COMPENSATION," by Henry A. Hill, the contents of which are incorporated herein in their entirety by reference.

Another example of a cyclic error compensation technique is described in U.S. Pat. No. 6,778,280, entitled "INTERFEROMETRY SYSTEM AND METHOD EMPLOYING AN ANGULAR DIFFERENCE IN PROPAGATION BETWEEN ORTHOGONALLY POLARIZED INPUT BEAM COMPONENTS," by Henry A. Hill and Peter de Groot, the contents of which are incorporated herein in their entirety by reference.

A further example of a cyclic error compensation technique is described in U.S. Pat. No. 6,806,962, entitled "TILTED INTERFEROMETER," by Henry A. Hill, the contents of which is herein incorporated in their entirety by reference.

Other techniques for cyclic error compensation include those described in U.S. Pat. No. 6,137,574 entitled "SYSTEMS AND METHODS FOR CHARACTERIZING AND CORRECTING CYCLIC ERRORS IN DISTANCE MEASURING AND DISPERSION INTERFEROMETRY;" U.S. Pat. No. 6,252,668 B1, entitled "SYSTEMS AND METHODS FOR QUANTIFYING NON-LINEARITIES IN INTERFEROMETRY SYSTEMS;" and U.S. Pat. No. 6,246,481, entitled "SYSTEMS AND METHODS FOR QUANTIFYING NONLINEARITIES IN INTERFEROMETRY SYSTEMS," wherein all three are by Henry A. Hill, the contents of the three above-cited patents and patent applications are herein incorporated in their entirety by reference.

Lithography Applications

As discussed, lithography tools are especially useful in lithography applications used in fabricating large scale integrated circuits such as computer chips and the like. Lithography tools are also used in fabricating flat panel display panels, such as liquid crystal display panels. Lithography is the key technology driver for the semiconductor manufacturing industry. Overlay improvement is one of the five most difficult challenges down to and below 100 nm line widths (design rules), see, for example, the *Semiconductor Industry Roadmap*, p. 82 (1997).

Overlay depends directly on the performance, i.e., accuracy and precision, of the distance measuring interferometers used to position the wafer and reticle (or mask) stages. Since a lithography tool may produce $50-100M/year of product, the economic value from improved performance distance measuring interferometers is substantial. Each 1% increase in yield of the lithography tool results in approximately $1 M/year economic benefit to the integrated circuit manufacturer and substantial competitive advantage to the lithography tool vendor. The methods and apparatus described above can improve overlay by reducing stage positioning errors associate with local refractivity variations in a lithography tool.

The function of a lithography tool is to direct spatially patterned radiation onto a photoresist-coated wafer. The process involves determining which location of the wafer is to receive the radiation (alignment) and applying the radiation to the photoresist at that location (exposure).

To properly position the wafer, the wafer includes alignment marks on the wafer that can be measured by dedicated sensors. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photochemical processes in the resist that convert the radiation pattern into a latent image within the resist.

Interferometry metrology systems, such as those discussed previously, are important components of the positioning mechanisms that control the position of the wafer and reticle, and register the reticle image on the wafer. If such interferometry systems include the features described above, the accuracy of distances measured by the systems can be increased and/or maintained over longer periods without offline maintenance, resulting in higher throughput due to increased yields and less tool downtime.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

Interferometry systems described above can be used to precisely measure the positions of each of the wafer stage and mask stage relative to other components of the exposure system, such as the lens assembly, radiation source, or support structure. In such cases, the interferometry system can be attached to a stationary structure and the measurement object attached to a movable element such as one of the mask and wafer stages. Alternatively, the situation can be reversed, with the interferometry system attached to a movable object and the measurement object attached to a stationary object.

More generally, such interferometry systems can be used to measure the position of any one component of the exposure system relative to any other component of the exposure system, in which the interferometry system is attached to, or supported by, one of the components and the measurement object is attached, or is supported by the other of the components.

Figure 3:
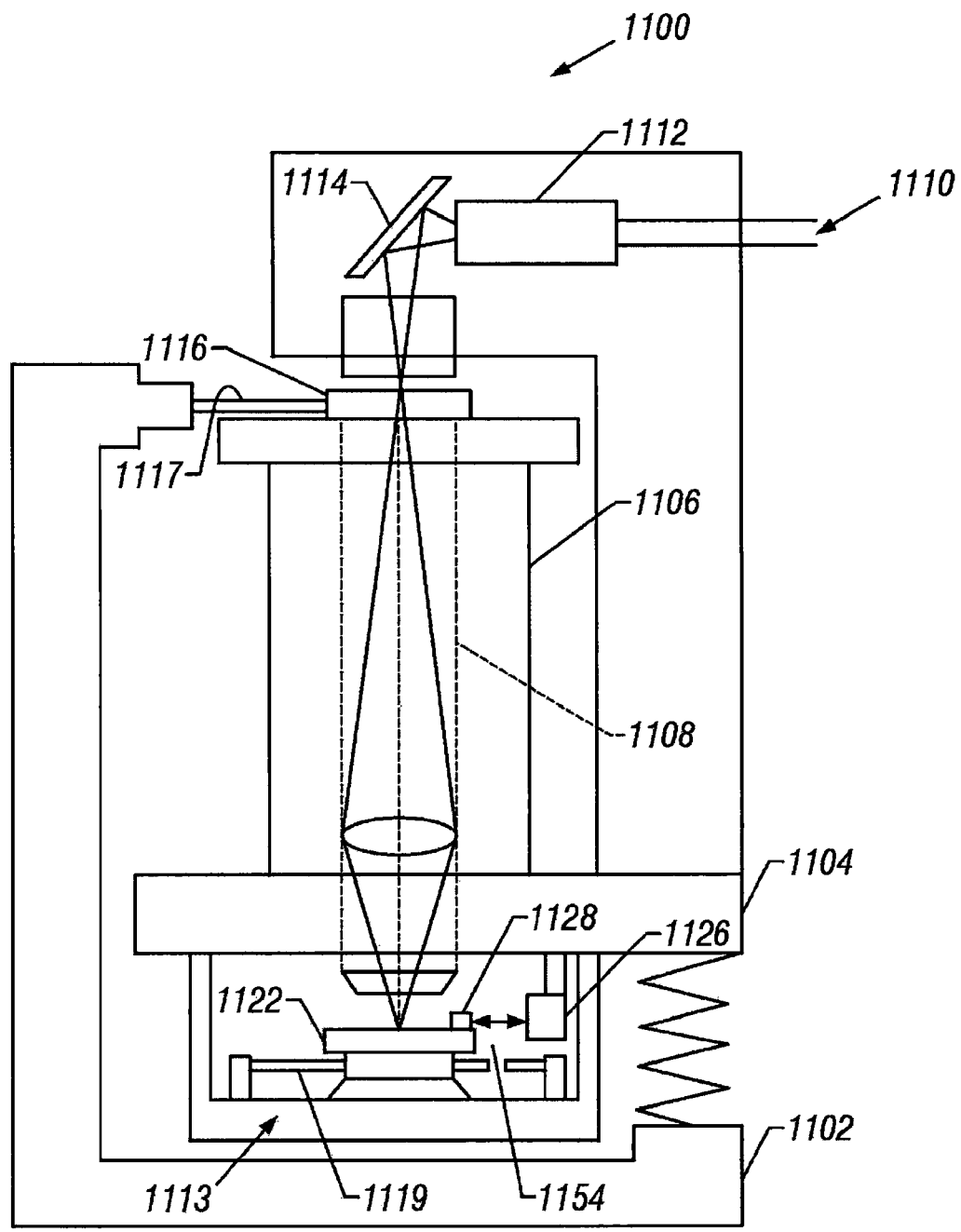
FIG. 3 is a schematic diagram of an embodiment of a lithography tool that includes an interferometer.

Another example of a lithography tool 1100 using an interferometry system 1126 is shown in FIG. 3. The interferometry system is used to precisely measure the position of a wafer (not shown) within an exposure system. Here, stage 1122 is used to position and support the wafer relative to an exposure station. Scanner 1100 includes a frame 1102, which carries other support structures and various components carried on those structures. An exposure base 1104 has mounted on top of it a lens housing 1106 atop of which is mounted a reticle or mask stage 1116, which is used to support a reticle or mask. A positioning system for positioning the mask relative to the exposure station is indicated schematically by element 1117. Positioning system 1117 can include, e.g., piezoelectric transducer elements and corresponding control electronics. Although, it is not included in this described embodiment, one or more of the interferometry systems described above can also be used to precisely measure the position of the mask stage as well as other moveable elements whose position must be accurately monitored in processes for fabricating lithographic structures (see supra Sheats and Smith *Microlithography: Science and Technology*).

Suspended below exposure base 1104 is a support base 1113 that carries wafer stage 1122. Stage 1122 includes a plane mirror 1128 for reflecting a measurement beam 1154 directed to the stage by interferometry system 1126. A positioning system for positioning stage 1122 relative to interferometry system 1126 is indicated schematically by element 1119. Positioning system 1119 can include, e.g., piezoelectric transducer elements and corresponding control electronics. The measurement beam reflects back to the interferometry system, which is mounted on exposure base 1104. The interferometry system can be any of the embodiments described previously.

During operation, a radiation beam 1110, e.g., an ultraviolet (UV) beam from a UV laser (not shown), passes through a beam shaping optics assembly 1112 and travels downward after reflecting from mirror 1114. Thereafter, the radiation beam passes through a mask (not shown) carried by mask stage 1116. The mask (not shown) is imaged onto a wafer (not shown) on wafer stage 1122 via a lens assembly 1108 carried in a lens housing 1106. Base 1104 and the various components supported by it are isolated from environmental vibrations by a damping system depicted by spring 1120.

In other embodiments of the lithographic scanner, one or more of the interferometry systems described previously can be used to measure distance along multiple axes and angles associated for example with, but not limited to, the wafer and reticle (or mask) stages. Also, rather than a UV laser beam, other beams can be used to expose the wafer including, e.g., x-ray beams, electron beams, ion beams, and visible optical beams.

In some embodiments, the lithographic scanner can include a column reference. In such embodiments, the interferometry system 1126 directs the reference beam (not shown) along an external reference path that contacts a reference mirror (not shown) mounted on some structure that directs the radiation beam, e.g., lens housing 1106. The reference mirror reflects the reference beam back to the interferometry system. The interference signal produce by interferometry system 1126 when combining measurement beam 1154 reflected from stage 1122 and the reference beam reflected from a reference mirror mounted on the lens housing 1106 indicates changes in the position of the stage relative to the radiation beam. Furthermore, in other embodiments the interferometry system 1126 can be positioned to measure changes in the position of reticle (or mask) stage 1116 or other movable components of the scanner system. Finally, the interferometry systems can be used in a similar fashion with lithography systems involving steppers, in addition to, or rather than, scanners.

Figure 4A:
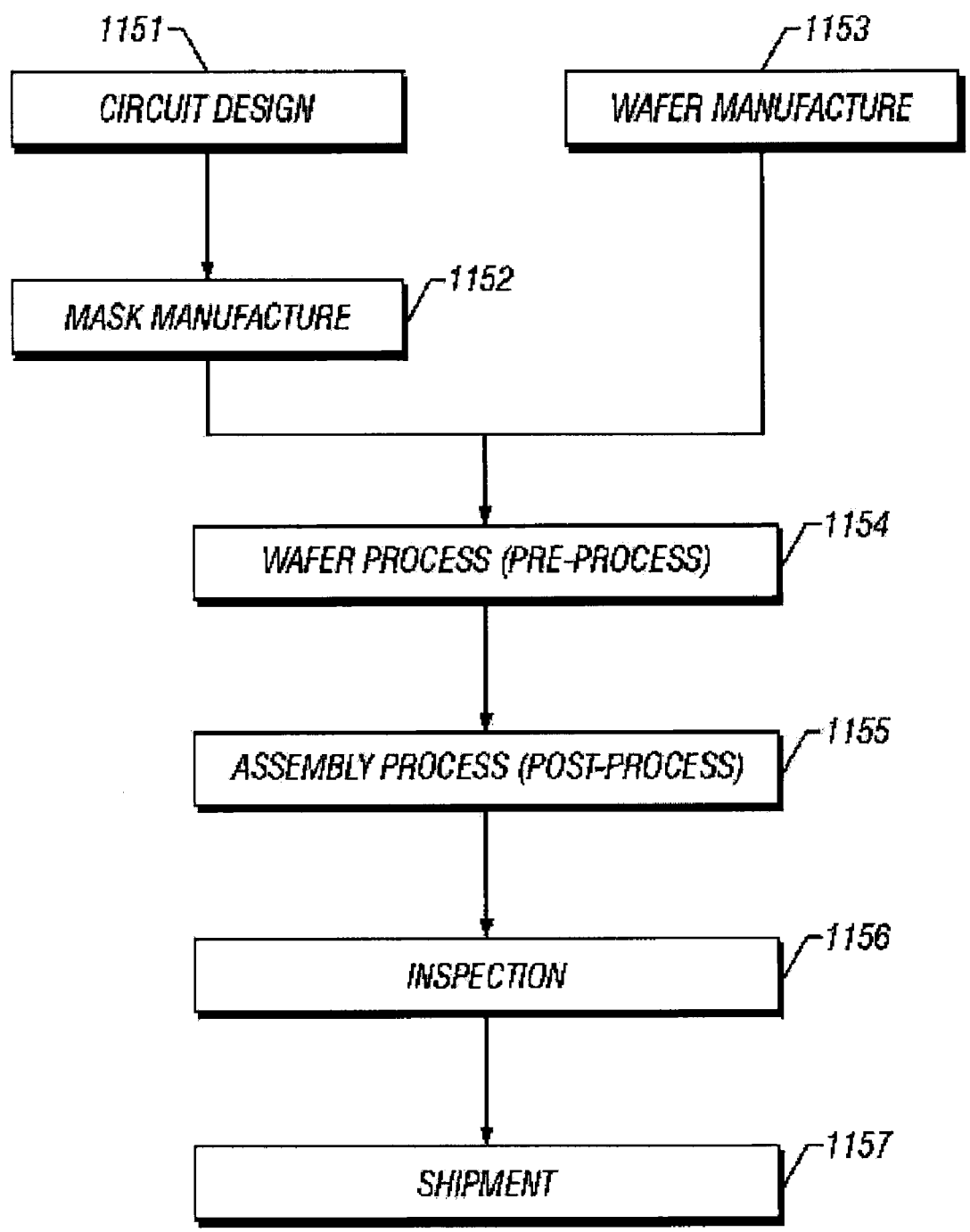
FIG. 4a and FIG. 4b are flow charts that describe steps for making integrated circuits.

As is well known in the art, lithography is a critical part of manufacturing methods for making semiconducting devices. For example, U.S. Pat. No. 5,483,343 outlines steps for such manufacturing methods. These steps are described below with reference to FIGS. 4a and 4b. FIG. 4a is a flow chart of the sequence of manufacturing a semiconductor device such as a semiconductor chip (e.g., IC or LSI), a liquid crystal panel or a CCD. Step 1151 is a design process for designing the circuit of a semiconductor device. Step 1152 is a process for manufacturing a mask on the basis of the circuit pattern design. Step 1153 is a process for manufacturing a wafer by using a material such as silicon.

Step 1154 is a wafer process which is called a pre-process wherein, by using the so prepared mask and wafer, circuits are formed on the wafer through lithography. To form circuits on the wafer that correspond with sufficient spatial resolution those patterns on the mask, interferometric positioning of the lithography tool relative the wafer is necessary. The interferometry methods and systems described herein can be especially useful to improve the effectiveness of the lithography used in the wafer process.

Step 1155 is an assembling step, which is called a post-process wherein the wafer processed by step 1154 is formed into semiconductor chips. This step includes assembling (dicing and bonding) and packaging (chip sealing). Step 1156 is an inspection step wherein operability check, durability check and so on of the semiconductor devices produced by step 1155 are carried out. With these processes, semiconductor devices are finished and they are shipped (step 1157).

Figure 4B:
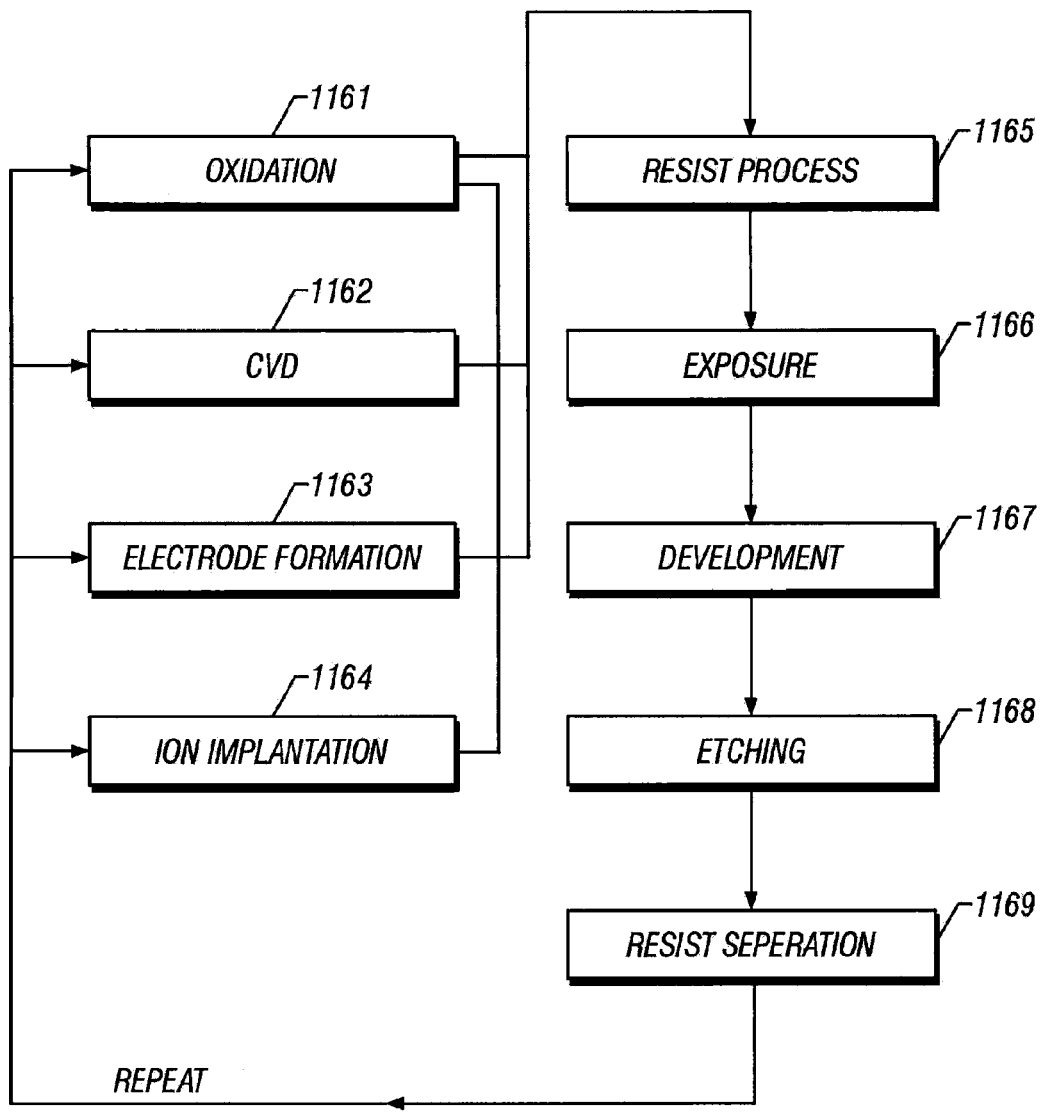

FIG. 4b is a flow chart showing details of the wafer process. Step 1161 is an oxidation process for oxidizing the surface of a wafer. Step 1162 is a CVD process for forming an insulating film on the wafer surface. Step 1163 is an electrode forming process for forming electrodes on the wafer by vapor deposition. Step 1164 is an ion implanting process for implanting ions to the wafer. Step 1165 is a resist process for applying a resist (photosensitive material) to the wafer. Step 1166 is an exposure process for printing, by exposure (i.e., lithography), the circuit pattern of the mask on the wafer through the exposure apparatus described above. Once again, as described above, the use of the interferometry systems and methods described herein improve the accuracy and resolution of such lithography steps.

Step 1167 is a developing process for developing the exposed wafer. Step 1168 is an etching process for removing portions other than the developed resist image. Step 1169 is a resist separation process for separating the resist material remaining on the wafer after being subjected to the etching process. By repeating these processes, circuit patterns are formed and superimposed on the wafer.

The interferometry systems described above can also be used in other applications in which the relative position of an object needs to be measured precisely. For example, in applications in which a write beam such as a laser, x-ray, ion, or electron beam, marks a pattern onto a substrate as either the substrate or beam moves, the interferometry systems can be used to measure the relative movement between the substrate and write beam.

Figure 5:
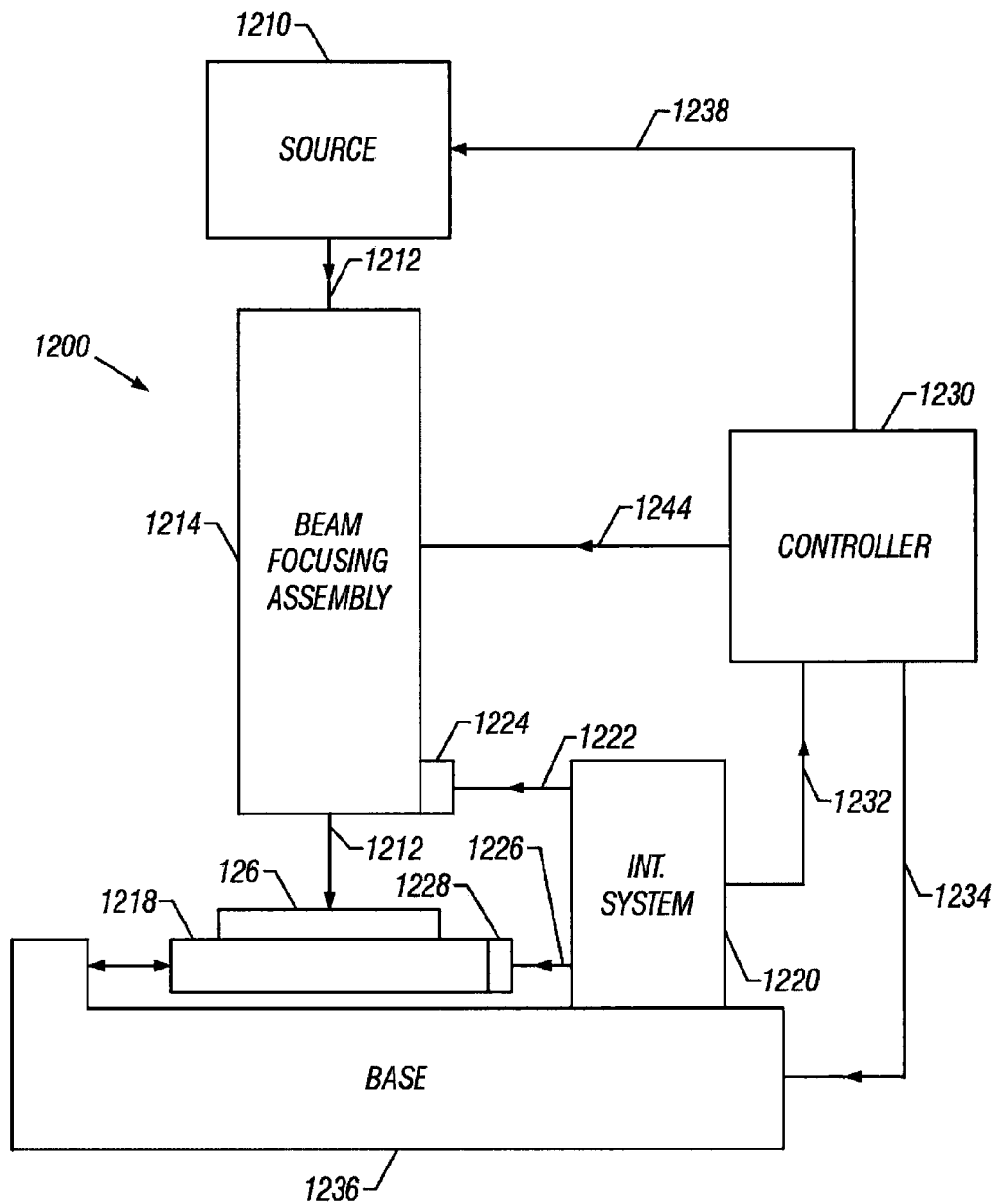
FIG. 5 is a schematic of a beam writing system that includes an interferometry system.

As an example, a schematic of a beam writing system 1200 is shown in FIG. 5. A source 1210 generates a write beam 1212, and a beam focusing assembly 1214 directs the radiation beam to a substrate 1216 supported by a movable stage 1218. To determine the relative position of the stage, an interferometry system 1220 directs a reference beam 1222 to a mirror 1224 mounted on beam focusing assembly 1214 and a measurement beam 1226 to a mirror 1228 mounted on stage 1218. Since the reference beam contacts a mirror mounted on the beam focusing assembly, the beam writing system is an example of a system that uses a column reference. Interferometry system 1220 can be any of the interferometry systems described previously. Changes in the position measured by the interferometry system correspond to changes in the relative position of write beam 1212 on substrate 1216. Interferometry system 1220 sends a measurement signal 1232 to controller 1230 that is indicative of the relative position of write beam 1212 on substrate 1216. Controller 1230 sends an output signal 1234 to a base 1236 that supports and positions stage 1218. In addition, controller 1230 sends a signal 1238 to source 1210 to vary the intensity of, or block, write beam 1212 so that the write beam contacts the substrate with an intensity sufficient to cause photophysical or photochemical change only at selected positions of the substrate.

Furthermore, in some embodiments, controller 1230 can cause beam focusing assembly 1214 to scan the write beam over a region of the substrate, e.g., using signal 1244. As a result, controller 1230 directs the other components of the system to pattern the substrate. The patterning is typically based on an electronic design pattern stored in the controller.

In some applications the write beam patterns a resist coated on the substrate and in other applications the write beam directly patterns, e.g., etches, the substrate.

An important application of such a system is the fabrication of masks and reticles used in the lithography methods described previously. For example, to fabricate a lithography mask an electron beam can be used to pattern a chromium-coated glass substrate. In such cases where the write beam is an electron beam, the beam writing system encloses the electron beam path in a vacuum. Also, in cases where the write beam is, e.g., an electron or ion beam, the beam focusing assembly includes electric field generators such as quadrapole lenses for focusing and directing the charged particles onto the substrate under vacuum. In other cases where the write beam is a radiation beam, e.g., x-ray, UV, or visible radiation, the beam focusing assembly includes corresponding optics and for focusing and directing the radiation to the substrate.

Other embodiments are in the following claims.

What is claimed is:

1. A method, comprising:
    using an interferometry assembly to provide three different output beams, each output beam comprising an interferometric phase related to an optical path difference between a corresponding first beam and a corresponding second beam, each first beam having the same wavelength and contacting a measurement object at least once;
    monitoring the interferometric phases for each of the three different output beams;
    deriving information about variations in the optical properties of a gas in the first beam paths from the three monitored phases;
    wherein deriving the information comprises determining a parameter based on the monitored interferometric phases for the three different output beams and removing a contribution to the parameter due to variations in the optical properties of the gas having a particular range of frequencies; and
    wherein the three monitored interferometric phases are each related to a respective first, second, and third displacement of the measurement object along a corresponding axis and the parameter is a second-difference parameter, SDP, which corresponds to a weighted difference between a first parameter and a second parameter, the first parameter being the difference between the first displacement and the second displacement and the second parameter being the difference between the third displacement and the first displacement.

2. The method of claim 1 wherein the information comprises a first contribution and a second contribution, the first and second contributions corresponding to variations in the optical properties of the gas at first and second frequencies, respectively.

3. The method of claim 2 wherein the first frequencies correspond to variations caused by turbulence in the first beam paths.

4. The method of claim 3 wherein the second frequencies correspond to variations caused by acoustic perturbations in the gas.

5. The method of claim 2 wherein the first frequencies are about 10 Hz or less.

6. The method of claim 5 wherein the second frequencies are about 100 Hz or more.

7. The method of claim 1 wherein the contribution to the parameter due to the variations having the particular range of frequencies are removed using a low pass filter.

8. The method of claim 1 wherein the contribution to the parameter due to the variations having the particular range of frequencies are removed using a high pass filter.

9. The method of claim 1 wherein deriving the information comprises determining a parameter based on the monitored interferometric phases for the three different output beams and determining a frequency transform of the parameter, wherein the three monitored interferometric phases are each related to a respective first, second, and third displacement of the measurement object along a corresponding axis and the parameter is a second-difference parameter, SDP, which corresponds to a weighted difference between a first parameter and a second parameter, the first parameter being the difference between the first displacement and the second displacement and the second parameter being the difference between the third displacement and the first displacement.

10. The method of claim 9 wherein deriving the information comprises calculating an average of the frequency transform over a band of frequencies corresponding to variations in the information caused by turbulence or acoustic perturbations in the first beam paths.

11. The method of claim 1 wherein deriving the information comprises determining a parameter based on the monitored interferometric phases for the three different output beams and determining coefficients of a series expansion of the parameter.

12. The method of claim 1 wherein the interferometer assembly defines three coplanar, parallel interferometer axes and each interferometric phase includes information about a position of the measurement object along a corresponding one of the interferometer axes.

13. The method of claim 1 wherein each of the first beams contact the measurement object more than once, wherein each of the first beams contact the measurement object at a common location for at least one of the passes to the measurement object.

14. The method of claim 1 wherein each of the second beams also contact the measurement object.

15. The method of claim 1 further comprising monitoring a degree of freedom of the measurement object from one of the interferometric phases, wherein deriving the information comprises reducing errors in the monitored degree of freedom, where the errors are related to the variations in the optical properties of a gas in the first beam paths.

16. The method of claim 15 further comprising reducing errors in the monitored degree of freedom due to stationary effects in the gas.

17. The method of claim 1 wherein the three monitored interferometric phases are each related to a respective first, second, and third displacement of the measurement object along a corresponding axis and deriving the information comprises determining values of a second difference parameter, SDP, from the monitored interferometric phases, where the SPD corresponds to a weighted difference between a first parameter and a second parameter, the first parameter being the difference between the first displacement and the second displacement and the second parameter being the difference between the third displacement and the first displacement, and determining a difference, $SDP_T$, between the second difference parameter value at time, t, and an average second difference parameter value.

18. The method of claim 1 further comprising using a lithography tool to expose a substrate supported by a moveable stage with radiation while interferometrically monitoring the position or orientation of the stage based on the derived information.

19. A system, comprising:
an interferometry assembly configured to provide three different output beams, each output beam comprising an interferometric phase related to an optical path difference between a corresponding first beam and a corresponding second beam, where the first beams each have the same wavelength and the interferometry assembly directs each first beam to contact a measurement object at least once;
three detectors each positioned in a path of a corresponding output beam;
an electronic processor coupled to the detectors, the electronic processor being configured to monitor the three interferometric phases and to derive information about variations in the optical properties of a gas in the measurement beam paths from the three monitored phases;
wherein deriving the information comprises determining a parameter based on the monitored interferometric phases for the three different output beams and removing a contribution to the parameter due to variations in the optical properties of the gas having a particular range of frequencies; and
wherein the three monitored interferometric phases are each related to a respective first, second, and third displacement of the measurement object along a corresponding axis and the parameter is a second-difference parameter, SDP, which corresponds to a weighted difference between a first parameter and a second parameter, the first parameter being the difference between the first displacement and the second displacement and the second parameter being the difference between the third displacement and the first displacement.

20. The system of claim 19 wherein the interferometry assembly is configured to direct each of the first beams to contact the measurement object more than once and to direct each of the second beams to contact the measurement object, wherein the first beams contact the measurement object at a common location for at least one of the passes to the measurement object.

21. The system of claim 19 wherein the interferometry assembly defines three different coplanar, parallel interferometer axes where the interferometric phase of each output beam corresponds to a position of the measurement object with respect to a corresponding one of the measurement axes.

22. The system of claim 19 further comprising a dispersion interferometer configured to monitor variations in the optical properties of the gas in the measurement beam paths,
wherein the dispersion interferometer is in communication with the electronic processor and the electronic processor is configured to determine a degree of freedom of the measurement object based on the variations in the optical properties of the gas monitored by the dispersion interferometer and from the information about variations in the optical properties of a gas in the measurement beam paths from the three monitored phases.

23. A lithography system for use in fabricating integrated circuits on a wafer, the system comprising:
the system of claim 19;
an illumination system for imaging spatially patterned radiation onto a wafer supported by the moveable stage; and
a positioning system for adjusting the position of the stage relative to the imaged radiation;
wherein the interferometer assembly is configured to monitor the position of the wafer relative to the imaged radiation and electronic processor is configured to use the information about to the variations in the optical properties of the gas to improve the accuracy of the monitored position of the wafer.

24. A method, comprising:
using an interferometry assembly to monitor a degree of freedom of a stage in a lithography system while exposing a wafer to radiation using the lithography system;
wherein monitoring the degree of freedom comprises:
using an interferometry assembly to monitor an interferometric phase of three different output beams, each interferometric phase being related to an optical path difference between a corresponding first beam and a corresponding second beam, each first beam having the same wavelength and contacting a measurement object at least once, and each interferometric phase being related to a position of a stage with respect to a component of the interferometry assembly located away from the stage;
deriving primary information about variations in the optical properties of a gas between the component and the stage;
using a dispersion interferometer to determine secondary information about variations in the optical properties of the gas in the lithography system;
determining the degree of freedom of the stage based on at least one of the interferometric phases, the primary information, and the secondary information;
wherein deriving primary information comprises determining a parameter based on the monitored interferometric phases for the three different output beams and removing a contribution to the parameter due to variations in the optical properties of the gas having a particular range of frequencies; and
wherein the three monitored interferometric phases are each related to a respective first, second, and third displacement of the measurement object along a corresponding axis and the parameter is a second-difference parameter, SDP, which corresponds to a weighted difference between a first parameter and a second parameter, the first parameter being the difference between the first displacement and the second displacement and the second parameter being the difference between the third displacement and the first displacement.

25. A system, comprising:
an illumination apparatus for imaging spatially patterned radiation onto a wafer supported by a moveable stage;
a positioning system for adjusting the position of the stage relative to the imaged radiation; and
an interferometry system comprising:
an interferometer assembly configured to provide multiple different output beams, each output beam comprising an interferometric phase related to an optical path difference between a corresponding first beam and a corresponding second beam, the first beams each having the same wavelength, where the interferometry assembly directs each first beam to contact a measurement object at least once;
multiple detectors each positioned in a path of a corresponding output beam;
an electronic processor coupled to the detectors, the electronic processor being configured to monitor the three interferometric phases and to derive primary information about variations in the optical properties of gas in the path of the first beams from the three monitored phases;
a dispersion interferometer configured to provide secondary information about variations in the optical properties of the gas, wherein the interferometry system is configured to monitor the position of the wafer relative to the imaged radiation and to use the information about the primary and secondary variations in the optical properties of the gas to improve the accuracy of the monitored position of the wafer;

wherein deriving primary information comprises determining a parameter based on the monitored interferometric phases for the multiple different output beams and removing a contribution to the parameter due to variations in the optical properties of the gas having a particular range of frequencies; and wherein the multiple monitored interferometric phases are each related to a respective first, second, and third displacement of the measurement object along a corresponding axis and the parameter is a second-difference parameter, SDP, which corresponds to a weighted difference between a first parameter and a second parameter, the first parameter being the difference between the first displacement and the second displacement and the second parameter being the difference between the third displacement and the first displacement.

* * * * *

UNITED STATES PATENT AND TRADEMARK OFFICE
CERTIFICATE OF CORRECTION

PATENT NO. : 7,826,063 B2  Page 1 of 1
APPLICATION NO. : 11/876577
DATED : November 2, 2010
INVENTOR(S) : Henry A. Hill It is certified that error appears in the above-identified patent and that said Letters Patent is hereby corrected as shown below:

Column 40, line 55 in claim 17, delete "SPD" insert --SDP--.

Signed and Sealed this
Eighteenth Day of January, 2011

David J. Kappos
*Director of the United States Patent and Trademark Office*